US006526160B1

(12) United States Patent
Ito

(10) Patent No.: US 6,526,160 B1
(45) Date of Patent: Feb. 25, 2003

(54) IRIS INFORMATION ACQUISITION APPARATUS AND IRIS IDENTIFICATION APPARATUS

(75) Inventor: Haruo Ito, Yokohama (JP)

(73) Assignee: Media Technology Corporation, Yokohama (JP)

( * ) Notice: Subject to any disclaimer, the term of this patent is extended or adjusted under 35 U.S.C. 154(b) by 0 days.

(21) Appl. No.: 09/350,142

(22) Filed: Jul. 9, 1999

(30) Foreign Application Priority Data

Jul. 17, 1998 (JP) .......................................... 10-219743

(51) Int. Cl.[7] ................................................ G06K 9/28
(52) U.S. Cl. ...................................... 382/117; 382/324
(58) Field of Search ................................ 382/117, 118, 382/124–127, 142, 312, 318, 319, 324; 356/71; 340/5.53, 5.83; 902/3, 6; 707/6; 713/186, 200; 250/208.6

(56) References Cited

U.S. PATENT DOCUMENTS

| | | | |
|---|---|---|---|
| 3,050,711 A | * 8/1962 | Harmon | 382/204 |
| 3,993,888 A | * 11/1976 | Fellman | 235/151 |
| 4,109,237 A | * 8/1978 | Hill | 340/146.3 E |
| 4,267,573 A | 5/1981 | Chaikin et al. | 364/515 |
| 4,641,349 A | 2/1987 | Flom et al. | 382/2 |
| 5,063,604 A | 11/1991 | Weiman | 382/41 |
| 5,291,560 A | 3/1994 | Daugman | 382/2 |
| 5,717,512 A | 2/1998 | Chmielewski, Jr. et al. | 359/210 |

FOREIGN PATENT DOCUMENTS

| | | | | |
|---|---|---|---|---|
| EP | 0 973 122 A2 | * 1/2000 | | G06K/9/20 |
| JP | 5297325 | 11/1993 | | G02B/27/46 |
| JP | 5297972 | 11/1993 | | G06E/3/00 |

OTHER PUBLICATIONS

Cheon Woo Shin et al., A New Anthropomorphic Retina-Like Visual Sensor, IEEE Pattern Recognition, 1994, vol. 3, pp. 345–348.*

"A Silicon Model of Early Visual Processing", C.A. Mead and M.A. Mahowald, Neural Networks, vol. 1. pp. 91–97, 1988.

* cited by examiner

Primary Examiner—Brian Werner
(74) Attorney, Agent, or Firm—Greenblum & Bernstein, P.L.C.

(57) ABSTRACT

An iris recognition system capable of remarkably reducing time taking from an image pickup of an iris image to generation of an iris code and of simplifying the construction is implemented. A sensor 10 comprises a group of pixels arranged in polar coordinates. An iris image is controlled so that the iris image is correctly formed on the sensor 10, particularly, the center of the iris image matches. The inner and outer diameters of the iris are detected according to the iris image formed on the sensor 10, and the difference between the inner diameter and the outer diameter in the radial direction is detected. The number i of pixels of each ring in the case of division into the predetermined number of concentric ring bands is calculated according to the difference. A weighted mean processing part 13 performs a weighted mean operation according to the number i of pixels. A band-pass filter 15 performs a processing in the tangential and radial directions of feature extraction of the iris image of each ring band and generates the iris code with a binary format formed by a binary circuit 16.

64 Claims, 15 Drawing Sheets

— Prior Art —

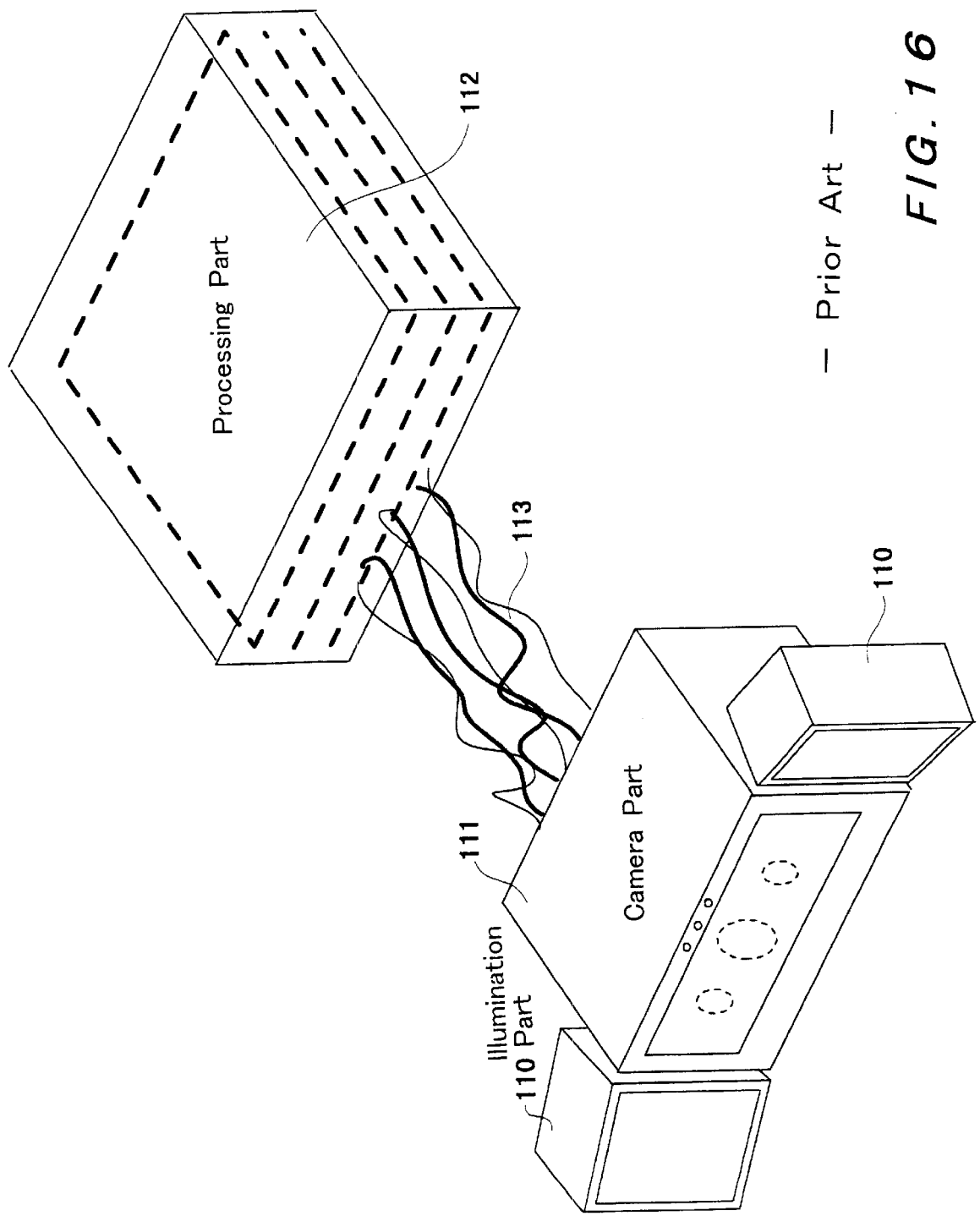
FIG. 16 — Prior Art —

IRIS INFORMATION ACQUISITION APPARATUS AND IRIS IDENTIFICATION APPARATUS

FIELD OF THE INVENTION

This invention relates generally to an iris information acquisition apparatus, an iris identification apparatus and the others, and particularly to techniques capable of remarkably reducing time from an image pickup of an iris image to generation of an iris code, and capable of simplifying the iris information acquisition apparatus, the iris identification apparatus and the like.

BACKGROUND OF THE INVENTION

Security systems accompanying development of high computerization in recent years require high reliability and convenience. In these security systems, for example, key, password, ID card, IC card, signature, voiceprints, fingerprints, biometric features (face pattern, set of teeth, retina, iris pattern and so on) are used as recognition means. Generally, in order of description of the above recognition means, degree of problems that these recognition means must be carried, are forgotten, are difficult to operate, are lost, are forged, etc. decreases, with the result that the recognition means have high reliability while the security systems become complicated and expensive.

The fingerprints among the above recognition means have been adopted by the police etc. of the whole world in the past and have been the most familiar personal identification means. However, a pattern of the fingerprints at the time of registration is not identical with that of the fingerprints at the time of matching since the fingertips are soft, and also, a false acceptance rate which is a probability of deciding the patterns identical in spite of the different patterns of the fingerprints and a false rejection rate which is a probability of deciding the patterns different in spite of the identical patterns of the fingerprints are said to become about 10 to 20% since the fingerprints themselves are easy to transform.

Also, in a system for matching a blood vessel pattern on the retina, to detect this blood vessel pattern, behavior of looking through a device for detecting the blood vessel pattern is forced and the false rejection rate becomes high due to influence of retinitis (hemorrhage of fundus oculi, white patch, exudation) and so on.

On the contrary, the iris pattern which has a demerit of hiding the iris in an eyelid is said to be almost immutable until death since two years of age, and a personal identification rate using the iris pattern has high reliability and thus, the iris pattern is said to be the most excellent personal identification system. As shown in FIG. 15, the iris means a region 101 having a pattern drawn radially on the outside of a pupil 100.

The personal identification system using such the iris pattern is disclosed in U.S. Pat. No. 5,291,560, for example. Also, an "IrisIdent" (registered trademark) system made of SENSAR Inc. in the U.S.A. is used as a practical system. As shown in FIG. 16, this system roughly comprises two illumination parts 110, a camera part 111, a processing part 112, and cables 113 for connecting the camera part 111 to the processing part 112. And then, the processing part 112 is connected to a host computer (not shown). A personal recognition processing using the system is generally performed according to the following procedure.

First, a three-dimensional position of the eye of human locating at the front of the camera part 111 is calculated on the basis of stereoscopic vision by two wide-angle cameras in the camera part 111. This calculation is performed by the processing part 112 on the basis of image pickup information fed from the wide-angle cameras.

Secondly, a zoom camera in the camera part 111 is focused on the three-dimensional position fed from the processing part 112 and zoom magnification is inversely proportioned to the distance.

Thirdly, by this, an iris image caught by the zoom camera is taken with a CCD image sensor of said zoom camera and is fed to the processing part 112.

Fourthly, the processing part 112 divides an iris portion (a region from the inner boundary to the outer boundary of the iris) in the taken iris image into eight concentric bands so as not to be influenced by variations in the pupil diameter. This is because the inside of the iris portion stretches and contracts in response to change in the pupil and thus the iris pattern itself stretches and shrinks. But, the outside of the iris portion does not change.

Fifthly, a convolution operation using a two-dimensional Gabor filter for feature extraction is performed every the divided band and a band-pass filtering is performed and the result is formed in binary code.

Sixthly, an iris code of 256 bits is calculated from the obtained binary information every the band.

Lastly, The processing part 112 performs personal identification by deciding whether the calculated iris code is matched with the previously registered iris code or not. This personal identification may be performed through the host computer (not shown) connected to the processing part 112.

In the personal identification system using the iris pattern mentioned above, however, the normal CCD image sensor arranged in a grid shape is used when the iris image is acquired, so that a coordinate of the iris portion of the iris image taken by the CCD image sensor must be transformed from an orthogonal coordinate system to a polar coordinate system and further, the convolution operation to each the transformed band must be performed. Since it takes an enormous time to process the coordinate transformation or the convolution operation, the is personal identification system had a problem that such the coordinate transformation or the convolution operation greatly affects a delay in processing time of the whole identification processing.

Although the above problem may be solved by enhancing the calculation capability of the processing part 112, a new problem has arisen in that the enhancement of the calculation capability requires a high cost naturally, and obstructs miniaturization and weight-saving of the personal identification system including the processing part 112.

SUMMARY OF THE INVENTION

Accordingly, it is an object of the present invention to provide an iris recognition and identification method and its system capable of removing the above-mentioned problems of the prior art.

It is another object of the present invention to provide an iris recognition and identification method and its system capable of remarkably reducing time required from image: pickup of an iris image to generation of an iris code as well as of simplifying the system.

It is yet another object of the present invention to provide an iris recognition and identification method and its system capable of remarkably reducing time required from image pickup of an iris image to generation of an iris code and further capable of simplifying the system.

According to an aspect of the present invention, there is provided an iris information sensor comprising an image pickup sensor having a group of photoelectric conversion pixels arranged in polar coordinates, wherein image light from an iris region of an eye is focused on the image pickup sensor so that the center of an iris image formed on the sensor substantially matches with the pole of the polar coordinates of the sensor and the photoelectric conversion pixels of the sensor are sequentially scanned to read out an iris image signal.

The image pickup sensor may be made of a group of pixels arranged in concentric circles.

The image pickup sensor may also be made of a group of pixels arranged in a spiral shape extending in the radial direction.

According to another aspect of the present invention, there is provided an iris information acquisition apparatus for obtaining image information of an iris region, comprising:

an image pickup sensor having a group of photoelectric conversion pixels arranged in polar coordinates;

image pickup optical system means for focusing image light from the iris region on the image pickup sensor;

optical axis operation control means for matching the center of an iris image formed on the sensor with the pole of the polar coordinates of the sensor;

region determination means for determining the iris region by acquiring the inner and outer diameters of the iris according to an iris image signal obtained by the sensor; and read scan means for scanning the determined iris region in a predetermined sequence and obtaining an output value corresponding to information of the iris region.

The read scan means for scanning the determined iris region may scan the determined iris region at least in the tangential direction.

The read scan means for scanning the determined iris region may scan the determined iris region in the tangential and radial directions every given width.

The read scan means may divide the determined iris region into predetermined concentric ring bands and determine the number of pixels of the radial direction of each ring band, and also read the output value corresponding to information of each ring band in which weighted mean is performed according to the number of pixels.

The region determination means may determine the iris region according to amplitude of a feature extraction signal, said feature extraction signal obtained by passing the image signal through a band-pass filter, said image signal obtained by scanning the image pickup sensor in the tangential direction.

The said region determination means may determine the iris region according to level variation in the image signal obtained by the scan in the radial direction of the image pickup sensor.

The optical axis operation control means may calculate the direction and size of an error between the center of the iris image formed on the image pickup sensor and the pole of the polar coordinates of the sensor to control a matching of the center of the iris image with the pole of the polar coordinates of the sensor, by further passing the feature extraction signal through a low-pass filter, said feature extraction signal obtained by passing the image signal through the band-pass filter, said image signal obtained by scanning the image pickup sensor in the tangential direction.

The iris information acquisition apparatus may further comprises illumination means for irradiating illumination light to the eye and a group of light receiving elements for receiving reflected light from the eye of the illumination light, the optical axis operation control means controlling a matching of the center of the iris image with the pole of the polar coordinates of the image pickup sensor according to an amount of receiving light of the group of light receiving elements.

According to still another aspect of the present invention, there is provided an iris information acquisition apparatus for obtaining image information of an iris region of an eye, comprising:

an image pickup sensor having a group of photoelectric conversion pixels arranged in polar coordinates;

image pickup optical system means for focusing image light from the iris region on the image pickup sensor;

illumination means for irradiating illumination light to the eye having the iris;

optical axis operation control means for matching the center of an iris image formed on the sensor with the pole of the polar coordinates of the sensor;

light adjustment control means for definitely controlling the inner diameter of the iris image formed on the sensor by irradiating visible light to the eye having the iris from the illumination means and adjusting an amount of the light and defining the pupil diameter; and read scan means for scanning the sensor in a predetermined sequence and reading image information of the iris region.

The image pickup optical system means may include a zoom lens and definitely keeps the outer diameter of the iris image formed on the image pickup sensor by the zoom lens.

The pixel of the image pickup sensor each may have a light receiving region with an approximately rhombic shape having each diagonal in the radial and tangential directions of the polar coordinates.

The pixel of the image pickup sensor each may also be arranged in a region with an approximately rhombic shape surrounded by the light receiving regions with the approximately rhombic shape.

The iris information acquisition apparatus may further comprise iris code generation means for generating an iris code according to the output value read by the read scan means.

The iris code generation means may comprise comparison means for comparing a band-pass filter receiving the output value and output of the band-pass filter with a predetermined threshold value.

The iris code generation means may generate the iris code by comparing the output value of a plurality of continuous pixels with output of a target pixel.

It is possible to add information on the effective range of the iris region to the iris code.

It is also possible to add information on resolution of the image pickup sensor to the iris code.

It is further possible to add information on tilt of the eye to the iris code.

It is further possible to add information on whether the iris code is the right eye or the left eye to the iris code.

The iris information acquisition apparatus may further comprises a group of light receiving elements for receiving reflected light from the eye of light irradiated by said illumination means, said optical axis operation control means controlling a matching of the center of the iris image with the pole of the polar coordinates of the image pickup sensor according to an amount of receiving light of the group of light receiving elements.

The optical axis operation control means may calculate the direction and size of an error between the center of the iris image formed on the image pickup sensor and the pole of the polar coordinates of the sensor to control a matching of the center of the iris image with the pole of the polar coordinates of the sensor, by further passing the feature extraction signal through a low-pass filter, said feature extraction signal obtained by passing the image signal through the band-pass filter, said image signal obtained by scanning the image pickup sensor in the tangential direction.

The optical axis operation control means may control a matching of the center of the iris image formed on the image pickup sensor by moving a mirror placed in an optical path between the eye of the iris of a subject and the sensor with the pole of the polar coordinates of the sensor.

The optical axis operation control means may control a matching of the center of the iris image formed on the image pickup sensor by moving the sensor with the pole of the polar coordinates of the sensor.

The optical axis operation control means may control a matching of the center of the iris image formed on the image pickup sensor by a vertical angle variable prism placed in an optical path between the eye of the iris of a subject and the sensor with the pole of the polar coordinates of the sensor.

The optical axis operation control means may control a matching of the center of the iris image formed on the image pickup sensor by mutually translating a plurality of lenses placed in an optical path between the eye of the iris of a subject and the sensor with the pole of the polar coordinates of the sensor.

The image pickup sensor may comprise a linear sensor in which pixels are arranged in the radial direction and rotation driving means for synchronously rotating the linear sensor around the pole of the polar coordinates, and a function equivalent to the group of the pixels of the polar coordinates may be achieved by the rotation of the linear sensor through the rotation driving means.

The pixel constructing the image pickup sensor each may be made of a MOS sensor or a CCD sensor.

The pixel constructing the image pickup sensor each may be made of a device for detecting edge information electrically or optically.

The pixel density in the radial direction of each pixel of the image pickup sensor may correspond to the rate of stretching and shrinking of the iris.

The image pickup sensor may be made of a group of pixels arranged in a spiral shape extending in the radial direction.

According to still another aspect of the present invention, there is provided an iris identification apparatus for acquiring an iris code representing information of an iris region of an eye and comparing and matching the acquired iris code with a previously registered iris code, comprising:

an image pickup sensor having a group of photoelectric conversion pixels arranged in polar coordinates;

image pickup optical system means for focusing image light from the iris region on the image pickup sensor;

optical axis operation control means for matching the center of an iris image formed on the sensor with the pole of the polar coordinates of the sensor;

region determination means for determining the iris region by acquiring the inner and outer diameters of the iris according to an iris image signal obtained by the sensor;

read scan means for dividing the determined iris region into predetermined concentric ring bands and determining the number of pixels of the radial direction of each ring band and reading the output value corresponding to information of each ring band in which weighted mean is performed according to the number of pixels;

iris code generation means for generating the iris code according to the output value; and comparison means for matching the generated iris code with the previously registered iris code.

The matching means may match the iris region including a region hidden by the eyelids.

The iris identification apparatus may further comprise a nonvolatile memory for storing the previously registered iris code, and means for encoding or ciphering the matched result in order to secure security.

The iris identification apparatus may further comprise means for adjusting identification determination level used when matching the generated iris code with the previously registered iris code.

According to still another aspect of the present invention, there is provided an iris identification apparatus for acquiring information of an iris region of an eye and comparing and matching the acquired information of the iris region with information of an iris region registered previously, comprising:

an image pickup sensor having a group of photoelectric conversion pixels arranged in polar coordinates;

image pickup optical system means for focusing image light from the iris region on the image pickup sensor;

illumination means for irradiating illumination light to the eye having the iris;

optical axis operation control means for matching the center of an iris image formed on the sensor with the pole of the polar coordinates of the sensor;

light adjustment control means for definitely controlling the inner diameter of the iris image formed on the sensor by irradiating visible light to the eye having the iris from the illumination means and adjusting an amount of the light and defining the pupil diameter;

read scan means for scanning the sensor in the tangential and radial directions and reading the information of the iris region; and matching means for matching the information of the iris region read by the read scan means with the information of the iris region registered previously through pattern matching.

The image pickup optical system means may include a zoom lens and definitely keeps the outer diameter of the iris image formed on the image pickup sensor by the zoom lens.

The matching means may match the iris region including a region hidden by the eyelids.

The iris identification apparatus may further comprise a nonvolatile memory for storing the previously registered iris code, and means for encoding or ciphering the matched result in order to secure security.

The iris identification apparatus may further comprise means for adjusting identification determination level used when said matching means performs said matching.

According to still another aspect of the present invention, there is provided an iris identification method for acquiring an iris code representing information of an iris region of an eye and comparing and matching the acquired iris code with a previously registered iris code, comprising the steps of:

using an image pickup sensor having a group of photoelectric conversion pixels arranged in polar coordinates;

focusing image light from the iris region on the image pickup sensor through image pickup optical system means;

matching the center of an iris image formed on the sensor with the pole of the polar coordinates of the sensor through optical axis operation control means;

determining the iris region by acquiring the inner and outer diameters of the iris according to an iris image signal obtained by the sensor;

dividing the determined iris region into predetermined concentric ring bands and determining the number of pixels of the radial direction of each ring band and reading the output value corresponding to information of each ring band in which weighted mean is performed according to the number of pixels;

generating the iris code from the output value through iris code generation means; and performing personal identification by matching the generated iris code with the previously registered iris code.

It is possible to match the iris region including a region hidden by the eyelids.

The previously registered iris code may be stored in a nonvolatile memory, and the iris identification method may further comprise the steps of encoding or ciphering the matched result in order to secure security.

It is possible to make identification determination level when performing personal identification adjustable from external or internally.

According to still another aspect of the present invention, there is provided an iris identification method for acquiring information of an iris region of an eye and comparing and matching the acquired information of the iris region with information of an iris region registered previously, comprising the steps of:

using an image pickup sensor having a group of photoelectric conversion pixels arranged in polar coordinates;

focusing image light from the iris region on the image pickup sensor through image pickup optical system means;

irradiating illumination light to the eye having the iris through illumination means;

matching the center of an iris image formed on the sensor with the pole of the polar coordinates of the sensor through optical axis operation control means;

definitely controlling the inner diameter of the iris image formed on the sensor by irradiating visible light to the eye having the iris from the illumination means and adjusting an amount of the light and defining the pupil diameter;

scanning the sensor in the tangential and radial directions and reading the information of the iris region through read scan means; and performing personal identification by matching the information of the iris region read by the read scan means with the information of the iris region registered previously through pattern matching.

The image pickup optical system means may include a zoom lens and may definitely keep the outer diameter of the iris image formed on the image pickup sensor by the zoom lens.

It is possible to match the iris region including a region or regions hidden by the eyelids.

It is possible to store the previously registered iris code in a nonvolatile memory, and may further comprise the steps of encoding or ciphering the matched result in order to secure security.

It is possible to make identification determination level when performing personal identification adjustable from external or internally.

BRIEF DESCRIPTION OF THE DRAWINGS

These and other features, and advantages, of the present invention will be more clearly understood from the following detailed description taken in conjunction with the accompanying drawings, in which like reference numerals designate identical or corresponding parts throughout the figures, and in which:

FIG. 16 is an illustration showing a schematic construction of a prior iris recognition system.

DESCRIPTION OF PREFERRED EMBODIMENTS

Figure 1:
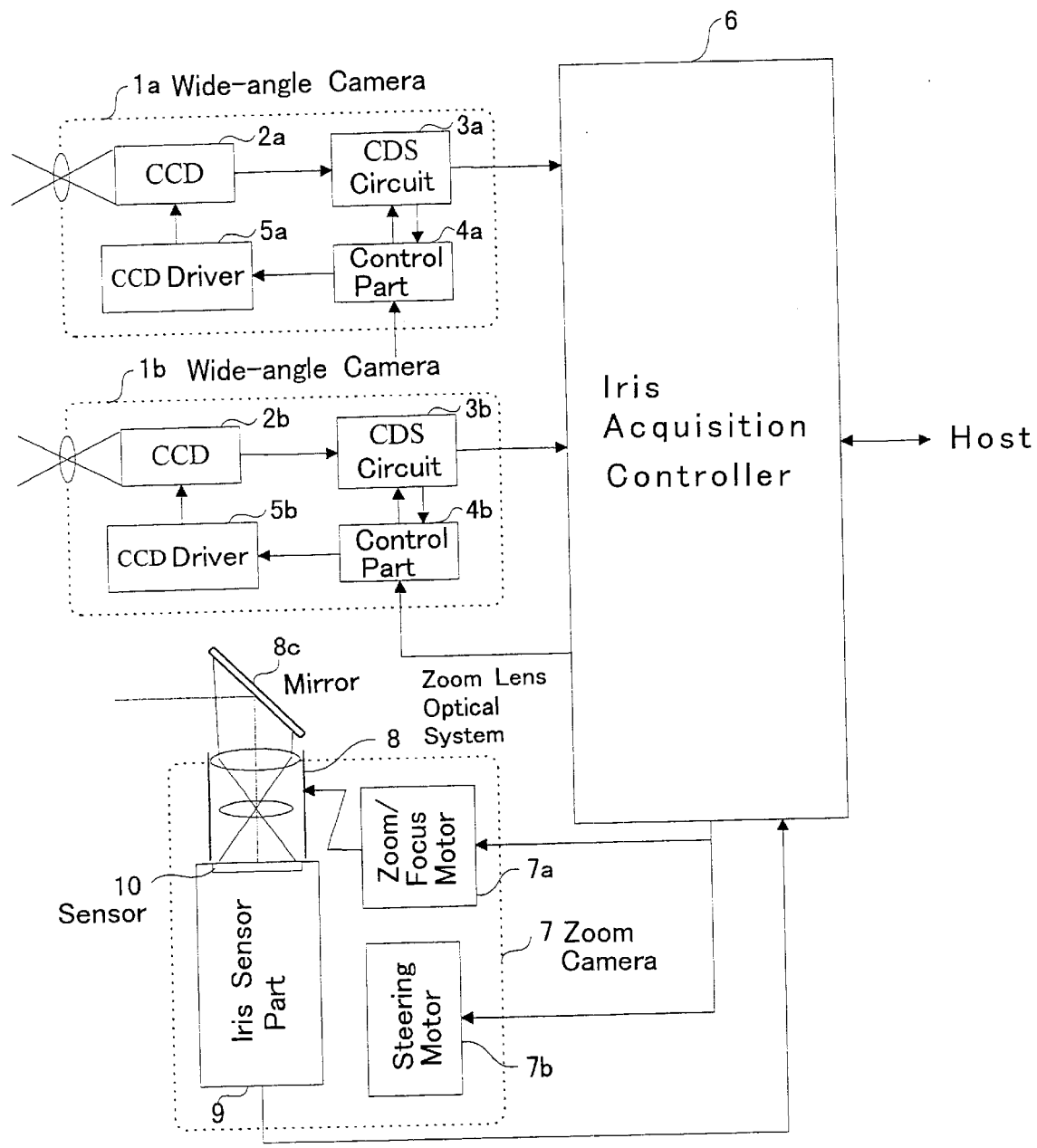
FIG. 1 is a block diagram showing the whole construction of an iris recognition system according to an embodiment of the present invention.

FIG. 1 shows the whole construction of an iris recognition system, namely, an iris information acquisition apparatus according to a first embodiment of the present invention. In FIG. 1, this iris recognition system includes two wide-angle cameras 1a, 1b and a zoom camera 7. The wide-angle cameras 1a and 1b take an image of a human eye of a subject of recognition by CCD's 2a and 2b, respectively, and image signals obtained by the CCD's 2a and 2b are fed to an iris acquisition controller 6 after reducing noise of the taken signal with CDS circuits 3a and 3b. Also, in the wide-angle cameras 1a and 1b, CCD drivers 5a and 5b for driving the CCDs 2a and 2b as well as a processing operation of the CDS circuits 3a and 3b are controlled on the basis of a synchronous control signal generated by control parts 4a and 4b.

Also, the system shown in FIG. 1 includes the iris acquisition controller 6 which specifies a three-dimensional position of the human eye of the subject of recognition according to an image signal inputted from the cameras 1a and 1b, and outputs signal or data indicating the specified result to the zoom camera 7.

The zoom camera 7 drives and controls a steering motor 7b to move a mirror 8c so that the image pickup direction of the zoom camera 7 is directed to the human eye according to the three-dimensional position obtained as mentioned above. Also, the zoom camera 7 controls a zoom/focus motor 7a for driving a zoom lens optical system 8 to be focused on the three-dimensional position of the human eye and regulates an amount of zoom so that an iris image of the pickup subject coincides with an image pickup region of a sensor 10. An iris sensor part 9 in the zoom camera 7 feeds position error and focus error information between the iris image taken by the sensor 10 and the sensor to the iris acquisition controller 6.

The iris acquisition controller 6 servocontrols each part of the camera system described above until information of the iris part described above is obtained. When the information of the iris part is obtained, this information, namely an iris code is matched with a previously registered iris code held within the iris acquisition controller 6 or held by a host computer (not shown). The matching may be performed either by the iris acquisition controller 6 or by the host computer. Also, the host computer may control each part of the camera system, or the sensor part itself may control each part by each error signal of the iris sensor part 9.

Here, the information of the iris part which the iris acquisition controller 6 receives from the iris sensor part 9 is an iris code formed in a binary form by the sensor part 9. A construction of this iris sensor part 9 will be described in detail with reference to FIGS. 2 and 3.

Figure 2:
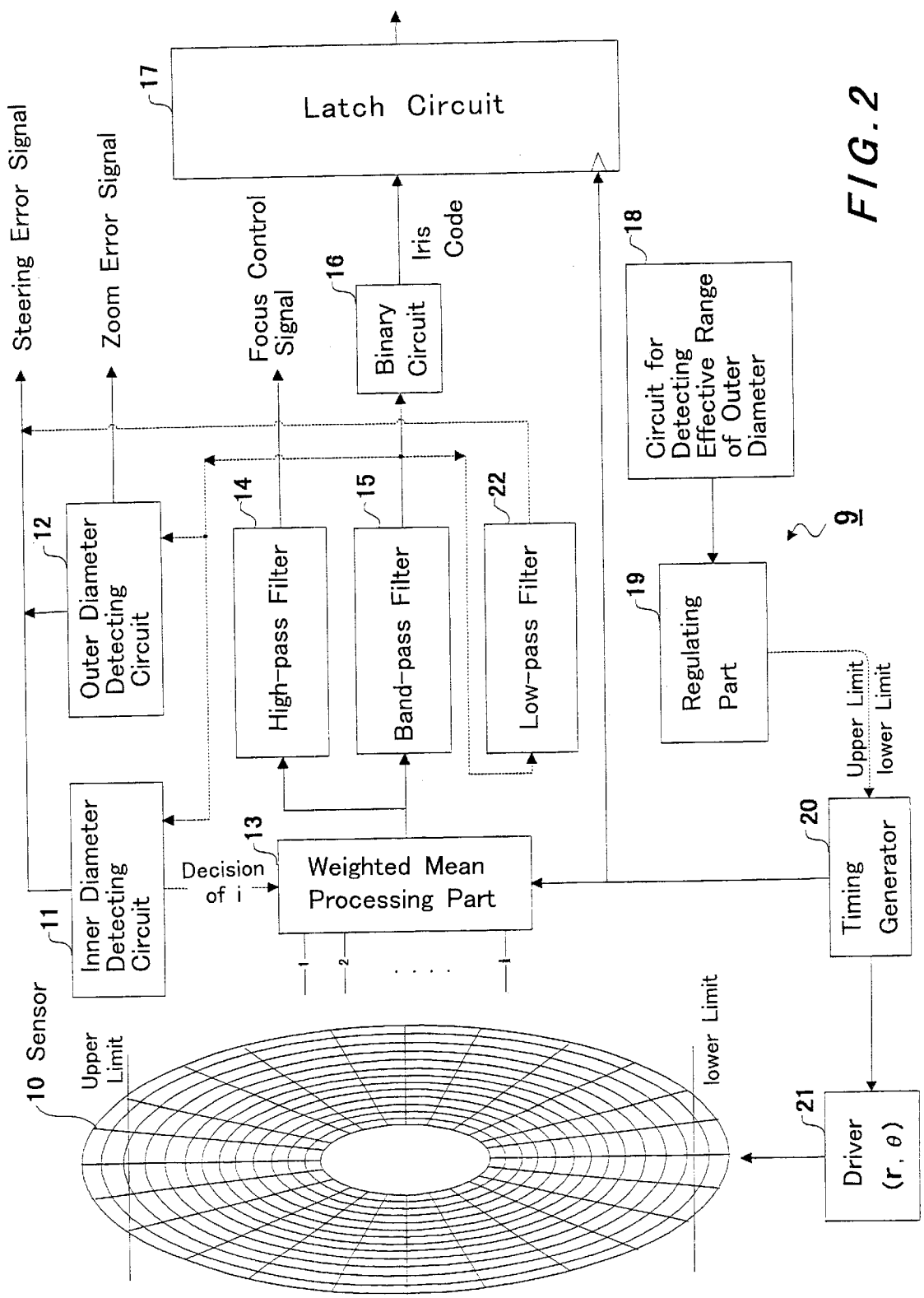
FIG. 2 is a block diagram showing a construction example of an iris sensor part of the iris recognition system according to the present invention.

FIG. 2 shows a detailed construction of the iris sensor part having the sensor 10. This sensor 10 has a pixel array pattern of polar coordinate type shown in FIG. 3, and each pixel has, for example, a shape partitioned by straight lines extending in the radial direction (r direction) and circumferential circles and light receiving areas of each pixel become larger as the pixel locates at the more outside of the radial direction. The sensor 10 may comprise CCD image sensors or MOS type image sensors. And, the shape of this pixel array pattern is suited for each ring shape in the case of acquiring the iris code.

The outer circumferential circle L1 of the pixel array pattern has the size so as to match with the outer circumference of the iris to be taken or become slightly larger than the outer circumference of the iris, when focusing and zooming control are performed, so that necessary resolution may be obtained when the iris image is taken.

The inner circumferential circle L2 has the size smaller than the size when the pupil becomes minimum, when the outer circumference of the iris matches with the circle L1. Since the pupil region always exists, the pixel array pattern has a region of a center part E1 surrounded by the circle L2. In this case, it is necessary to control alignment with the center of the iris and that of the pixel array pattern, since the iris image is taken by the sensor 10 having the pixel array pattern of polar coordinate type shown in FIG. 3.

A circuit 11 (FIG. 2) for detecting the inner diameter of the iris detects the boundary between the iris and the pupil of the radial direction in the taken iris image through the level variation, that is, an edge detection is performed, with the result that the inner diameter of the iris is calculated. On the other hand, a circuit 12 for detecting the outer diameter of the iris detects the outer circumference of the iris in the taken iris image through the level variation, that is, the edge detection is performed, with the result that the outer diameter is calculated. Then, the detecting circuits 11 and 12 output a steering error signal, namely a signal for indicating a position error of image formation to the iris acquisition controller 6 according to positions of the inner and outer diameters of the iris. Also, the outer diameter detecting circuit 12 outputs a zoom error signal to the iris acquisition controller 6.

Also, on the assumption that the outer diameter of the iris has matched with the outer diameter of the sensor 10 (the outer circumferential circle L1), the inner diameter detecting circuit 11 calculates the difference between the outer diameter of the sensor 10 and the detected inner diameter to calculate the number of pixels of the radial direction of the sensor 10 corresponding to said difference, and the value obtained by dividing this number of pixels by the number of ring bands (for example, 8) is fed to a weighted mean processing part 13 as the number i of pixels of the radial direction assigned to one ring. For example, the number i of pixels is set to "3" in FIG. 3.

Also, the outer diameter of the iris image may not always be matched with the outer diameter of the sensor 10. In this case, a zoom optical system is unnecessary and the number i of pixels is calculated on the basis of the difference between the outer diameter detected by the outer diameter detecting circuit 12 and the inner diameter detected by the inner diameter detecting circuit 11, but the outer diameter of the sensor 10 must be larger than the outer diameter of the iris image.

Figure 3:
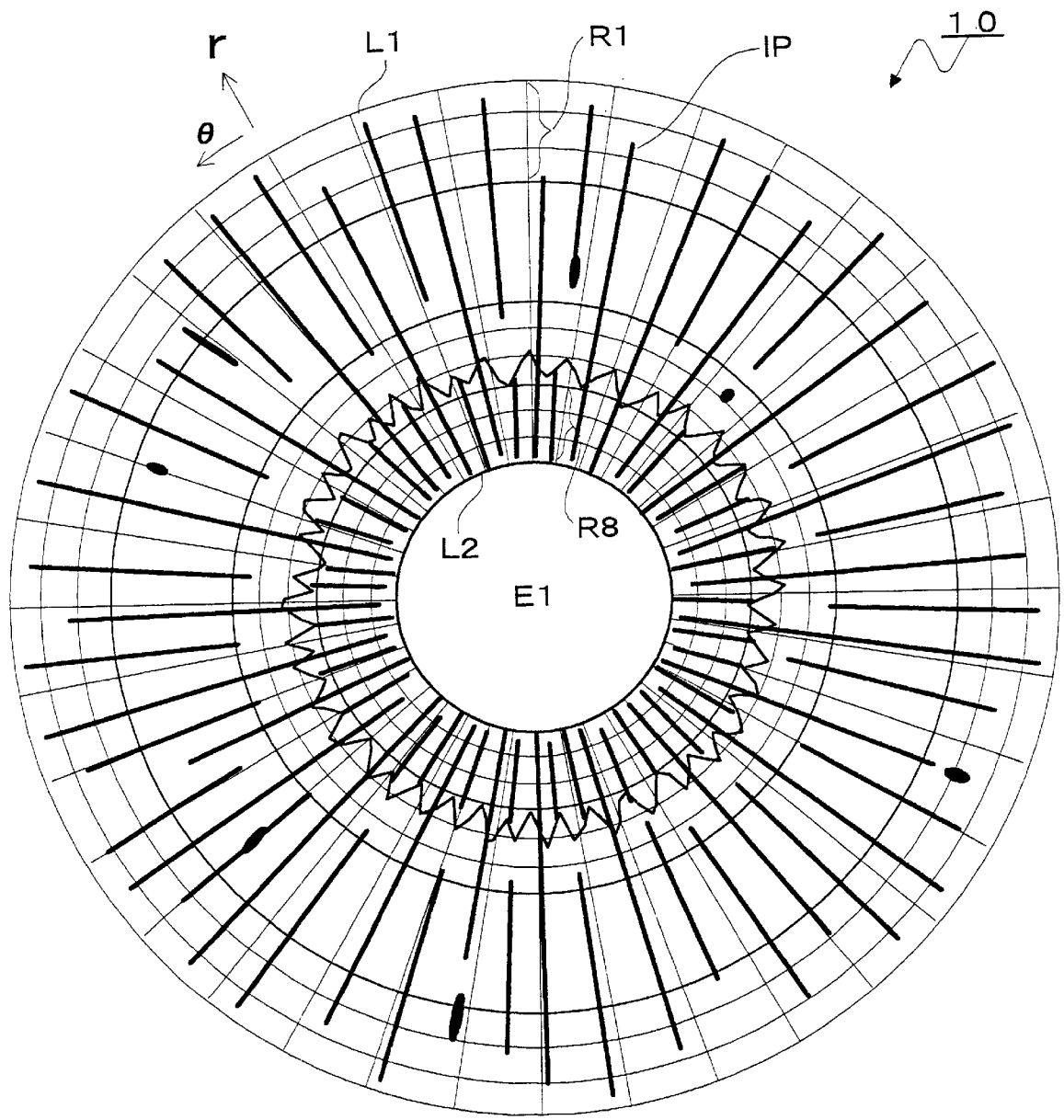
FIG. 3 is an illustration showing an example of a sensor.

The weighted mean processing part 13 calculates a weighted mean of pixel output signals of the number i of pixels when receiving the pixel output signals from the number i of pixels. The reason why this weighted mean is calculated is because the size of the pixel becomes larger as the pixel of the sensor 10 locates at the more outside as shown in FIG. 3, so that compensation of sensitivity variation caused by the increase in the light receiving area must be performed, and influence caused by a slight error of the dividing position of each ring and a steering error due to variation in the pupil diameter is decreased by performing the weighting to the center of each ring.

The value calculated by the weighted mean processing part 13 is fed to a high-pass filter 14 as an image output signal. The level or magnitude of high pass component of the image output signal from the high-pass filter 14 is taken out and is outputted as a focus control signal.

These steering error signal, zoom error signal and focus control signal are respectively fed to the iris acquisition controller 6. As described above, the controller 6 controls the steering motor 7b and the zoom/focus motor 7a in the zoom camera 7 so that the iris of the image pickup subject is matched with the center of the sensor 10 as well as the outer diameter of the iris is matched with the outer circumference of the sensor 10, and the focusing is performed.

A timing generator 20 drives a driver 21 of the sensor 10 and performs a scanning for outputting the pixel signals in the θ direction (rotational direction) every ring. When it becomes in the condition capable of taking a correct image by performing a fine adjustment by a feedback processing mentioned above, the signal outputted from each pixel is calculated or operated by the weighted mean processing part 13 to perform the weighted mean as described above and is fed to a band-pass filter 15. The band-pass filter extracts the change point in the fed pixel output signal, namely the signal change in the θ direction of the iris pattern. Further, a binary circuit 16 generates an iris code formed in a binary format, by performing conversion of the extracted signal into binary signal by a built-in comparator. Then, this iris code is fed to the iris acquisition controller 6 through a latch circuit 17.

As described above, the controller 6 compares the iris code of each ring band with the iris code previously registered in the host computer and so on so that a personal identification is performed. Also, the iris code may preferably be ciphered or encoded in order to secure security to transmit between each circuit device.

Also, since the upper and lower portions of the iris are hidden by eyelids generally, a circuit 18 for detecting effective range of the outer diameter of the iris detects the boundary between the eyelids and the iris through the level variation in the radial direction to calculate the upper and lower limits of the iris to be taken.

A regulating part 19 controls, for example, the timing generator 20 so as to invalidate the range beyond these upper and lower limits. For example, in the case of a MOS sensor, addressing in the range beyond the limits may be skipped.

Also, assuming that the image exists even in the portion hidden by the eyelids, the hide may be ignored. In this case, since a feature pattern does not exist in the eyelid portion, some degree of correlation decreases due to the matching of comparison between the eyelids when identifying the iris, but it does not matter.

Also, by adding information on the upper and lower limits to, for example, a header of the iris code, only the effective iris codes or the effective code portions in the iris code are compared each other when comparing the iris codes and thus, influence of the eyelids may be removed. That is, only the effective portions out of the registered iris codes are used as a comparison subject. Of course, when the iris codes are registered, the eye is preferably opened wide so that the iris is not hidden by the eyelids as wide as possible.

Further, by adding information on resolution, for example, data for indicating the number of pixels every circumference of the sensor or the number of ring bands to the header of the iris code, comparison between the iris codes obtained by the sensors having different resolutions may be readily performed.

Of course, by adding error-detecting codes such as checksum or CRC code to, for example, a footer of the iris code, reliability on the registered iris codes may be improved. Also, the above header and footer may be added to the iris codes registered or the iris codes obtained from the sensor 10, or both the iris codes.

Here, the comparison of the iris codes will be described in further detail. The comparison may be performed as an exclusive OR (EXOR) operation simply, unless a tilt of the eye exists, but the tilt exists generally so that the registered iris code is correlated with the detected iris code and it is determined whether a person having the detected iris code is the registered person or not, on the basis of the value with the highest correlation. This correlation may be performed by selecting the value with the highest correlation out of the values obtained when the position at θ=0° of the detected iris code is varied in the range of ±10°, for example.

So-called "hill-climbing" method etc. is used as a method for varying and obtaining a start point of comparison, and the correlation values shifted by one point back and forth are compared each other and the climbing is performed in the direction of higher correlation. On the contrary, the iris codes may be compared immediately without a correlation processing in the case of comparison if the tilt of the θ direction of the eye to be taken can be detected.

Figure 15:
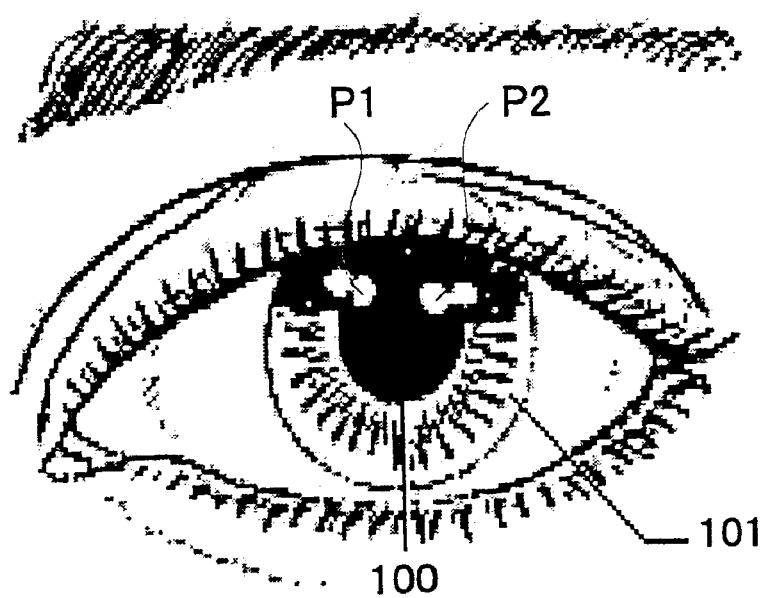
FIG. 15 is an illustration showing the position of the iris.

Also, the tilt of the eye, namely the tilt of the face may be grasped as a tilt to the horizontal plane formed by straight lines connecting bright points (P1 or P2 etc. in FIG. 15) of illumination reflected in both eyes to be taken by the wide-angle cameras 1a and 1b, correctly the horizontal plane (at θ=0°) of the zoom camera 7.

Thus, by storing information, in the header of the iris code, on whether the iris code is registered with the tilt of the eye compensated or is registered without the tilt of the eye compensated for example in case of single eye registration such as a peeping method, it is unnecessary to perform a useless correlation processing so that the comparison speed may be improved.

Also, by adding information on which eye is registered to the header, it is unnecessary to decide which eye is registered in the case of binocular registration so that the comparison speed may be improved.

Here, output of the band-pass filter 15 may be used, as another embodiment of the circuits 11 and 12 for detecting the inner and outer diameters of the iris, so that the inner and outer diameters of the iris may be detected readily. Also, by adding the low-pass filter 22 and using output of this filter 22, the steering error signal may be outputted readily. By performing feedback of this steering error signal directly to the steering motor 7b, steering of the zoom camera 7 may be servocontrolled directly.

Figure 4A:
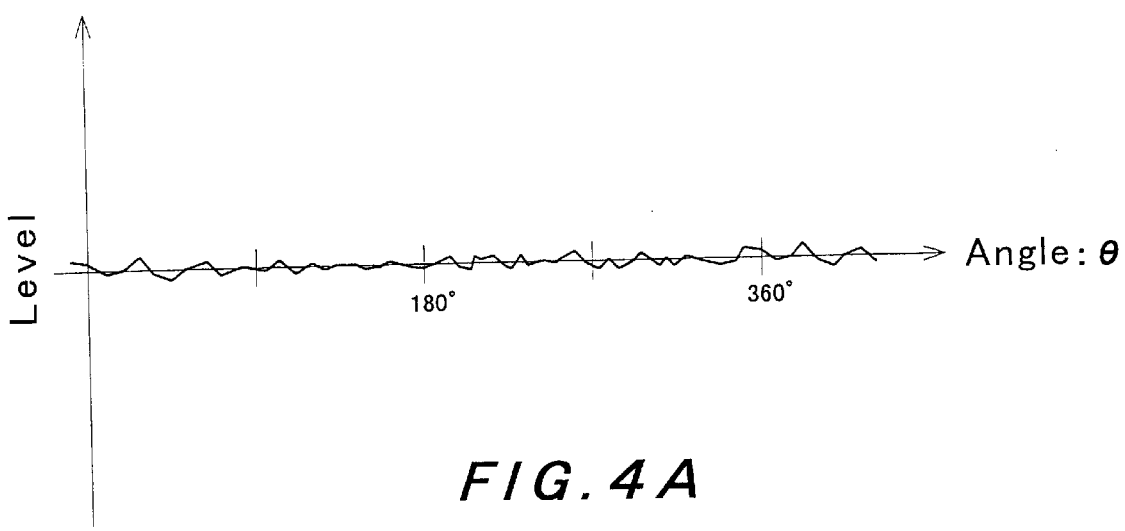
FIGS. 4A through FIG. 4C are waveform charts showing behavior of an output signal level with respect to an angle θ outputted from a band-pass filter 15 and a low-pass filter 22 of FIG. 2.

That is, when the driver 21 scans the pixel signal of the sensor 10 from the inner circumference of the sensor 10 to the outside in the radial direction, first, the output signal level from the band-pass filter 15 is almost zero regardless of an angle θ of the rotation direction as shown in FIG. 4A.

Figure 4B:
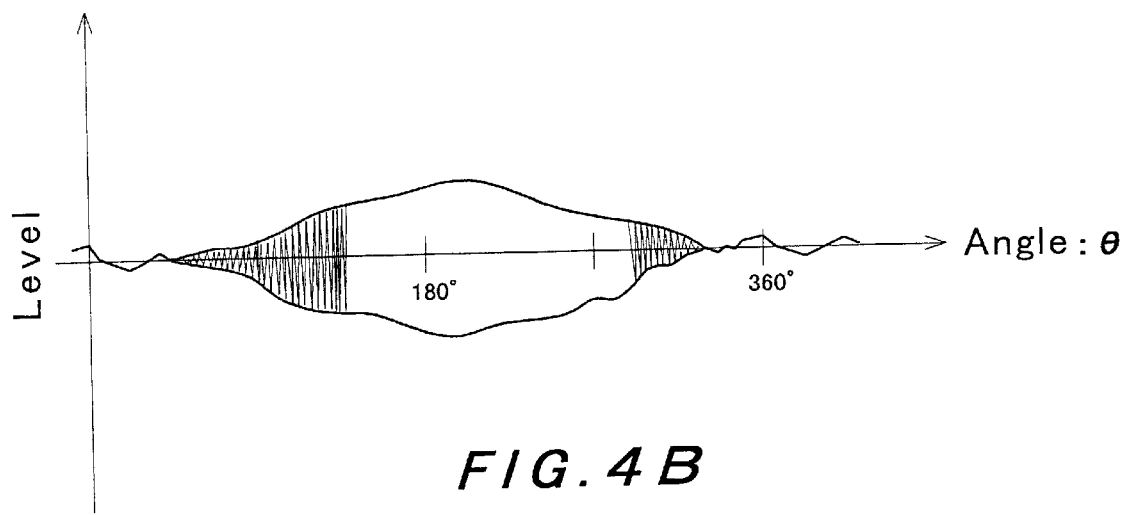

Subsequently, when the pixel signal is scanned in the radial direction gradually, the output signal level indicating detection of the iris portion appears as shown in FIG. 4B, and this output signal is a signal depending on an iris pattern of the iris portion. Further, when the pixel signal is scanned in the radial direction, the output signal level is saturated to a certain level and gradually approaches inclination determined by the ratio of light receiving area of each pixel as shown in FIG. 4C.

Therefore, the circuit 11 for detecting the inner diameter of the iris detects the position on the sensor 10 as the inner diameter of the iris, when the output signal level from the band-pass filter 15 has become a certain level, for example, the output signal level has appeared or has reached saturation. Similarly, the circuit 12 for detecting the outer diameter of the iris may detect the outer diameter of the iris through the fact that the output signal level from the band-pass filter 15 has become a predetermined level lower from the certain level or has become a level equal to or lower than a predetermined level. But, in the case of scanning to the outside in the radial direction, the scanning position, for example, immediately before the output signal level has become the certain level or lower is detected as the outer diameter of the iris.

Of course, the scanning may be performed from the outer circumference of the sensor 10 to the inside in the radial direction. Also, it is possible to calculate the inner diameter of the iris by the scanning to the outside in the radial direction, and to calculate the outer diameter by the scanning to the inside in the radial direction, so that the inner and outer diameters may be obtained at higher speed in this manner. By using the output signal from the band-pass filter 15 thus, the inner and outer diameters of the iris may be detected readily without a complex image processing.

Figure 4C:
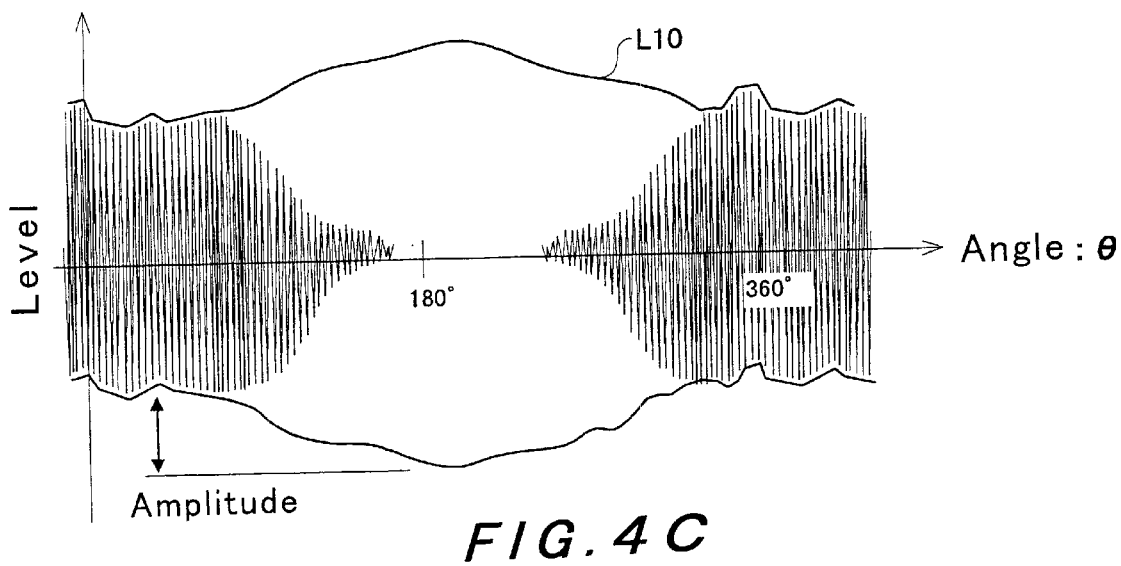

Further, as shown in FIG. 4C, an envelope L10 of the output signal level for the angle θ of the rotational direction may vary with respect to the angle θ of the rotational direction, and level variation in this envelope L10 means that the zoom camera 7 is not directed to the eye of the image subject. Thus, by providing the low-pass filter 22, the signal of an envelope level of the scanned image signal may be outputted and the level difference of this signal may be used as the steering error signal. In this case, also, the steering error signal may be outputted by a simple processing without using a complex image processing. In addition, the steering may be servocontrolled directly using this steering error signal.

Also, in FIG. 2, the band-pass filter 15 and the low-pass filter 22 receive the signal through the weighted mean processing part 13 and perform a filtering, but a direct pixel signal from the sensor 10 is preferably used, after filtering, as the signal fed to the inner and outer detecting circuits 11 and 12.

Thus, in the first embodiment, since the sensor 10 is constructed in pixel arrangement having the pixel array pattern of polar coordinate type shown in FIG. 3, a processing for transforming the orthogonal coordinate system into the polar coordinate system in the case of acquiring the image signal by the sensor having the pixel arrangement of orthogonal coordinate type is eliminated so that a processing speed for acquiring the iris code may be improved remarkably.

Also, although the pixel array pattern shown in FIG. 3 has the same distance between the radii of concentric circles so as to have the same length of pixel in the radial direction, the length of pixel in the radial direction may be varied according to the rate of stretching and shrinking of the iris. That is, the rate of stretching and shrinking of the iris depends on a thickness of the iris, and normally the thickness of the iris is thinner toward the center of iris and the iris is easy to stretch and shrink, so that the length of pixel of the radial direction in the pixel close to the center may be lengthened according to this nature of the iris. By varying the length of pixel of the radial direction thus, rate of recognition may be improved.

Figure 5:
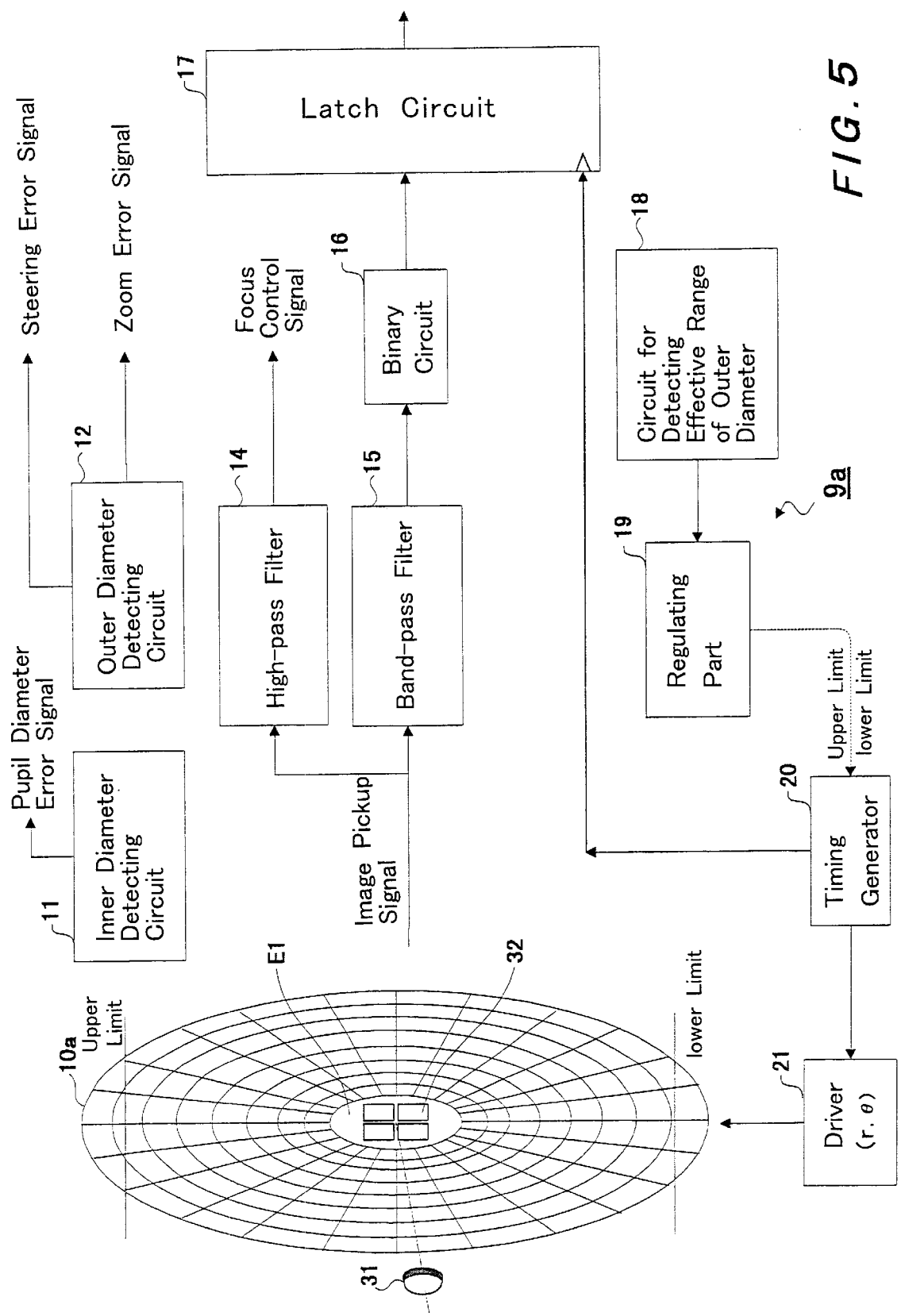
FIG. 5 is a block diagram showing an alternate construction example of the iris sensor part of the iris recognition system according to the present invention.

Next, a second embodiment will be described with reference to FIG. 5. FIG. 5 shows a construction of an iris sensor part 9a of an iris recognition system according to the second embodiment. The iris sensor part 9a is different from the iris sensor part 9 shown in FIG. 2 in that a sensor 10a is used instead of the sensor 10 and a construction of the weighted mean processing part 13 is eliminated. The other constructions are the same as those of the first embodiment and have the same reference characters as those of the first embodiment.

The sensor 10a has pixel arrangement of a pixel array pattern of polar coordinate type like the sensor 10 and has an illuminating LED 31 (light emitting diode) which is placed on an optical axis of the sensor and illuminates the eye of human with visible light. Also, it is favorably constructed so that the LED 31 may illuminate the eye of human exactly by shifting the position of a light emitting plane of the LED 31 optically from a light receiving plane of the sensor 10a. Also, an EL (electroluminescence) device etc. other than the LED 31 may be used as illumination means.

On the contrary, the circuit 11 for detecting the inner diameter of the iris detects the inner diameter of the iris, and the difference between this detected inner diameter and the inner circumference of the sensor 10a, namely a pupil diameter error signal is generated and is fed to the iris acquisition controller 6.

The iris acquisition controller 6 controls brightness of the LED 31 so as to eliminate the pupil diameter error signal. That is, this control is to increase the brightness of the LED 31 when the pupil diameter is longer than the inner circumference of the sensor 10a and to decrease the brightness of the LED 31 when the pupil diameter is shorter than the inner circumference of the sensor 10a.

By the above control, the pupil diameter always matches with the inner circumference of the sensor 10a and the outer circumference of the sensor 10a matches with the outer diameter of the iris through the steering error signal, the zoom error signal, etc. so that an iris portion of an image subject is taken with the iris portion always matching with the pixel array pattern on the sensor 10a.

Thus, the width in the radial direction of each pixel in the sensor may be determined based on necessary resolving power, so that for example, the length of the sensor in the radial direction may be divided into eight portions equally, and an iris code may be generated directly using an image pickup signal from the sensor 10a.

Also, since division to each ring band is unnecessary and the center of the iris is determined, a recognition processing may be performed with a very simple pattern matching by previously registering an iris image. That is, since the inner and outer diameters of the iris are known, the pattern matching may be performed only by rotation at the center of the iris so that a comparison speed may be improved considerably.

Also, In FIG. 5, means for detecting a position error is constructed by providing an array of photodiodes 32 in the center of the sensor 10a so that steering of the zoom camera 7 may be controlled. That is, light emitted by the LED 31 is reflected on the surface of the eye and is received by the photodiodes 32. The steering control is performed by using the difference between the amounts of light reception in the array position of each photodiode 32 as a steering error signal to feed the difference to the iris acquisition controller 6.

By using the array of the photodiodes 32 by which the center portion E1 is utilized usefully, the difference between the amounts of light reception may be employed instead of generating the steering error signal in the inner detecting circuit 11. Particularly, output of the array of the photodiodes 32 is fed back to the steering motor 7b directly and analogue servocontrol may be performed so that miniaturization and weight-saving of the system may be improved.

Figure 6:
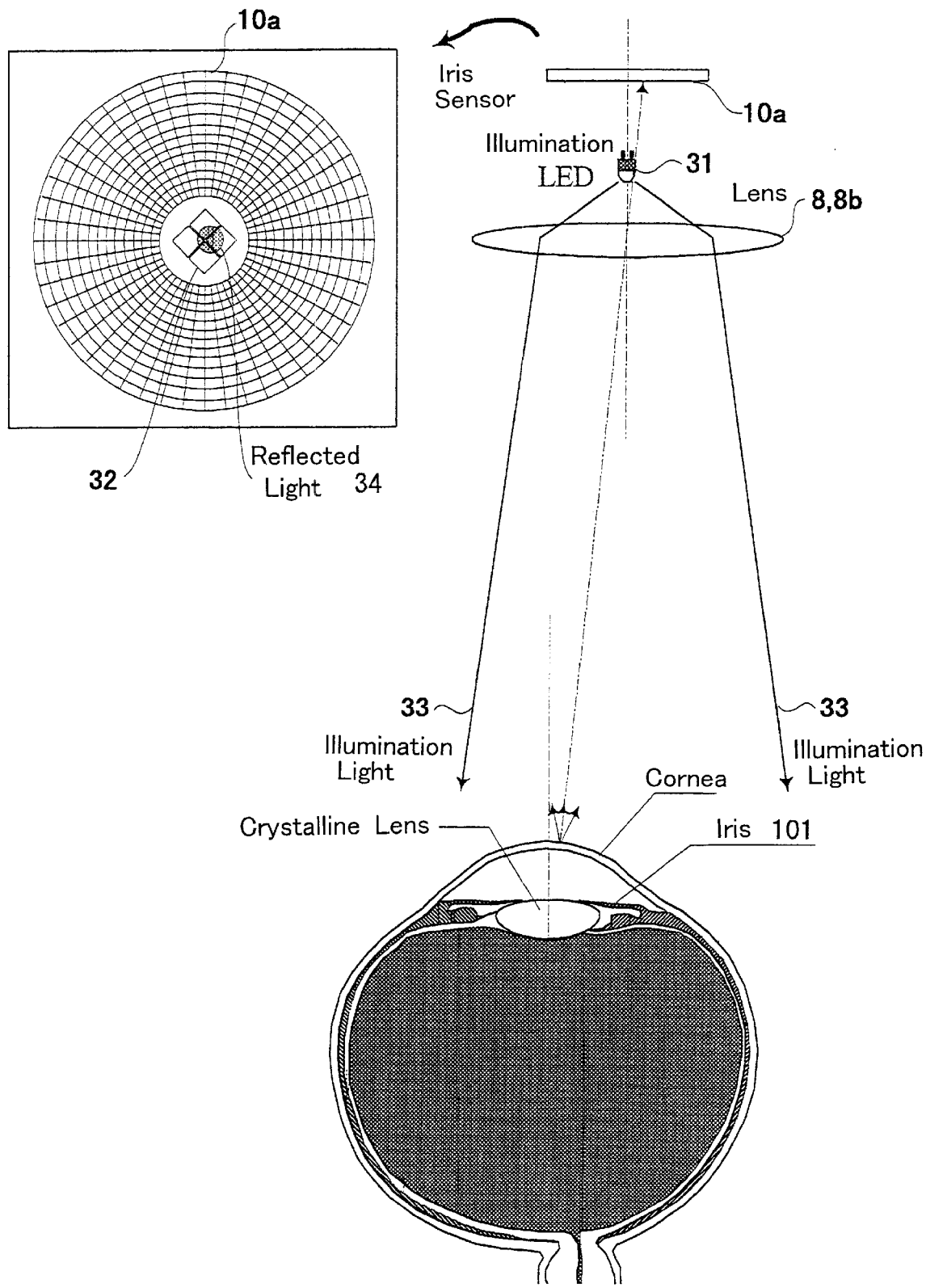
FIG. 6 is an illustration showing a use condition of the iris sensor part in FIG. 5.

Further, FIG. 6 shows an example of a position relationship of the eye to the sensor 10a etc. in the apparatus of FIG. 5. As shown in FIG. 6, illuminating light 33 emitted from the illuminating LED 31 is irradiated to the eye through an image pickup lens 8b. The pupil diameter of the eye is controlled according to the intensity of this irradiated light. The image of the iris having the controlled pupil diameter is formed on the sensor 10a through the image pickup lens 8b. Also, reflected light 34 indicates the situation that the reflected light from the LED 31 is irradiated on the photodiodes.

Moreover, the photodiodes 32 described above are preferably arranged in the proximity of the optical axis of the center of the sensor 10a and may also be provided outside the outer circumference of the pixel array pattern. In this case, the LED 31 may be arranged in the outside of the optical axis pairing with the photodiodes 32, for example.

Also, in the above-mentioned first embodiment as shown in FIG. 2, a light emitting device for emitting invisible light such as infrared rays (IR) and the photodiodes 32 for receiving reflected light from this light emitting device may be provided in the same position as the LED 31 and so on of the second embodiment. The means for detecting a position error is constructed by a combination of such a light emitting device and the photodiodes 32, and the steering error signal is obtained so that positioning of the iris image and the sensor 10 may be performed.

Next, a modification of the second embodiment will be described with reference to FIG. 7. The pixel array pattern of the sensor 10a constructing the second embodiment was the pixel array pattern of polar coordinate type like the sensor 10 and was a set of pixels each having a kind of approximately rectangular shape with the pattern divided by the straight lines of the radial direction every predetermined angle and the concentric circles every predetermined radius.

Figure 7:
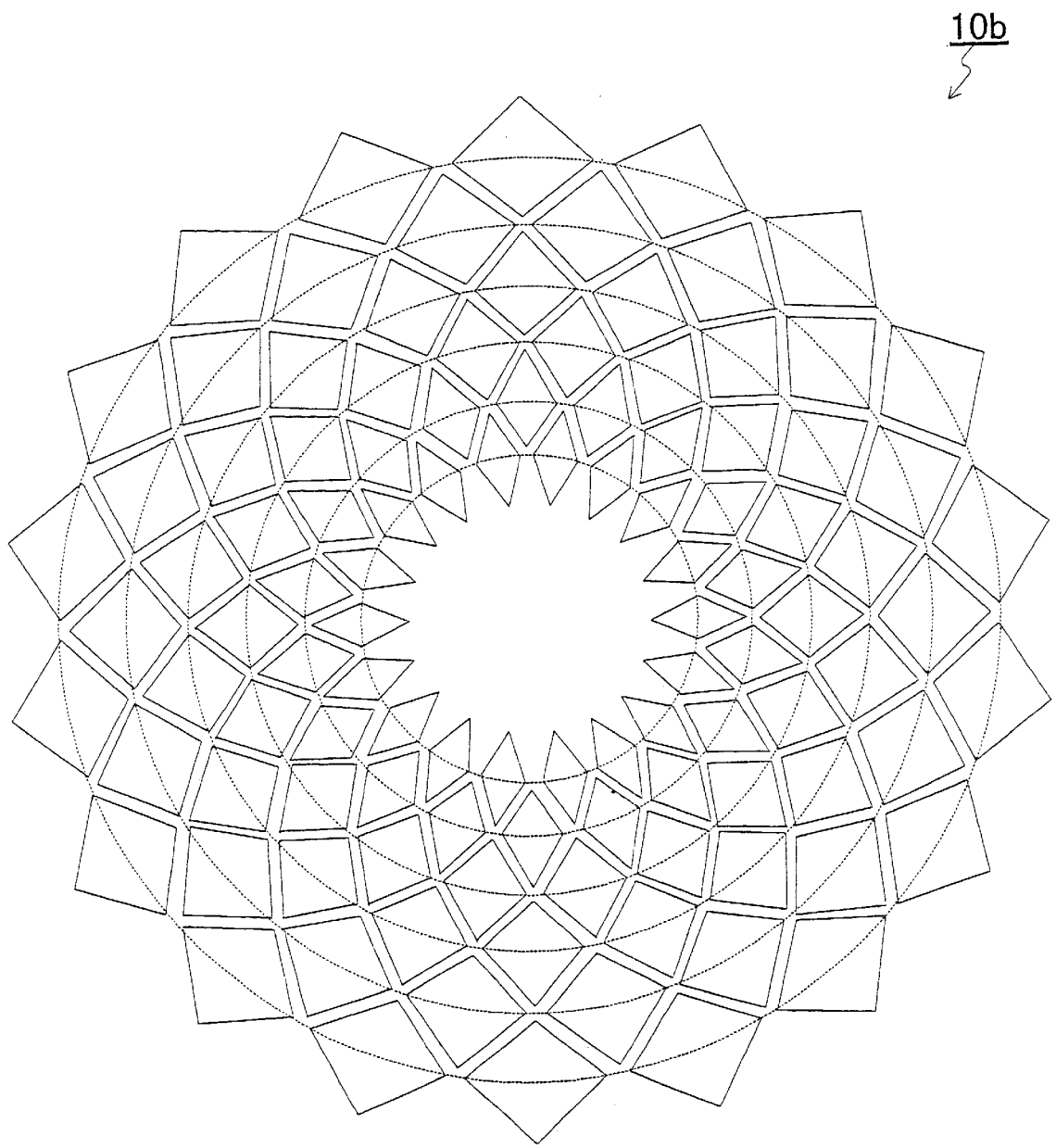
FIG. 7 is a plan view showing a construction example of a sensor.

On the contrary, in this modification, a sensor 10b has the pixel array pattern which is polar coordinate type and is a set of pixels of an approximately rhombic shape having each diagonal, in the circumferential direction and the radial direction as shown in FIG. 7. But, in this pixel array pattern, since a space exists between the pixels due to each pixel with the rhombic shape, the rhombic pixels are disposed also in this space so as to effectively utilize the space. Thus, the rhombic pixels on a concentric circle deviates from the rhombic pixels on other concentric circle adjacent this in the θ direction by half pixel mutually, and resolution may be improved. Of course, a construction in which the pixels are not buried in the space between the pixels may be used. Also, the shape of the pixel is not limited to the rhombic shape.

By using the pixel array pattern having the rhombic pixels with each diagonal in the circumferential direction and the radial direction, each pixel may automatically perform weighting in sensitivity within each ring band in the radial direction, from the shape itself of the light receiving part and output the weighted value. The degree of the weighting does not increase the false rejection rate so that the false rejection rate will be suppressed even if there is some steering error, namely the center of the sensor 10b deviates from the center of the iris image in some degree.

Figure 8:
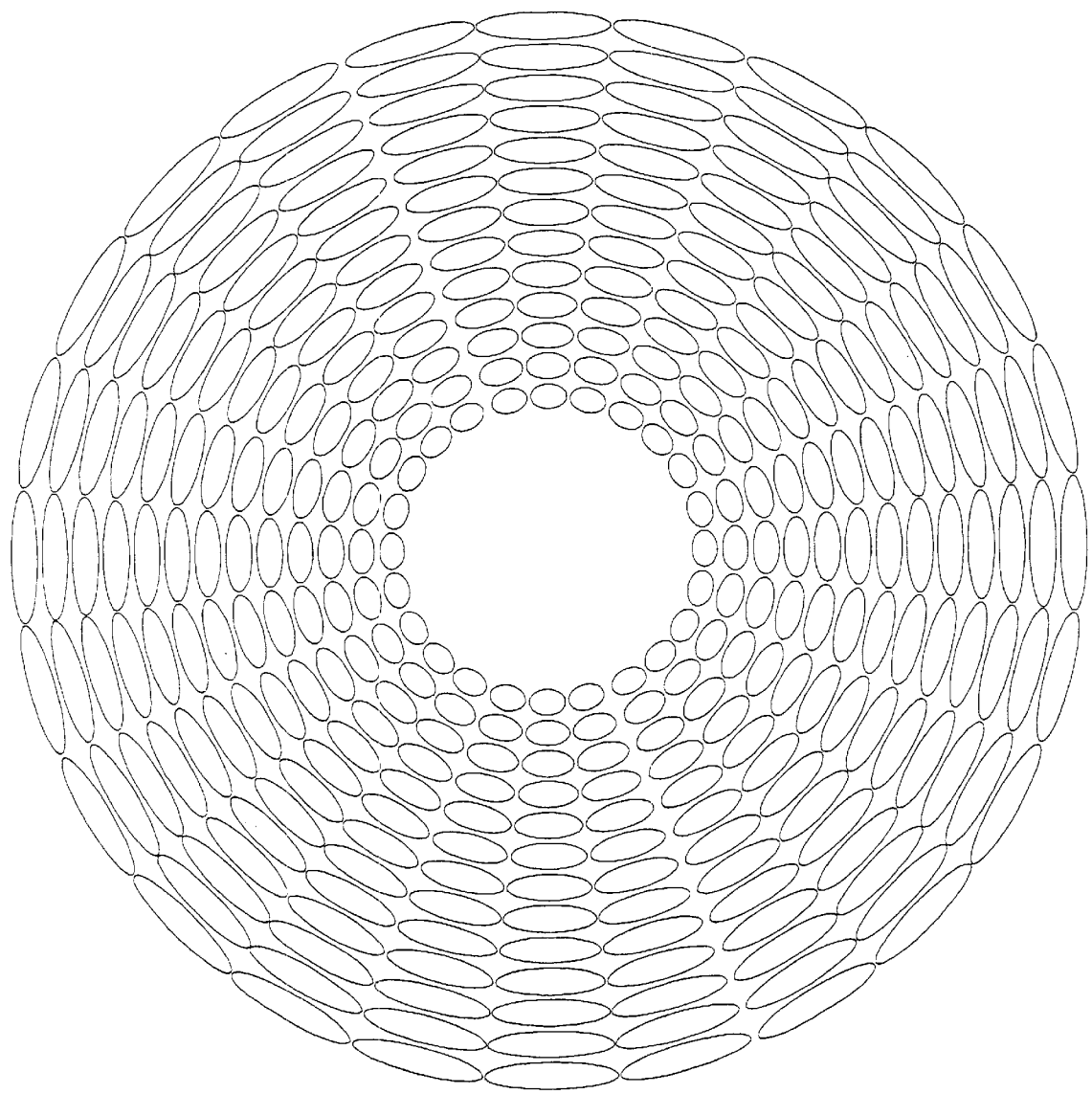
FIG. 8 is a plan view showing another construction example of the sensor.

Also, FIG. 8 shows an example of a sensor in which each pixel has an elliptic shape.

Figure 9:
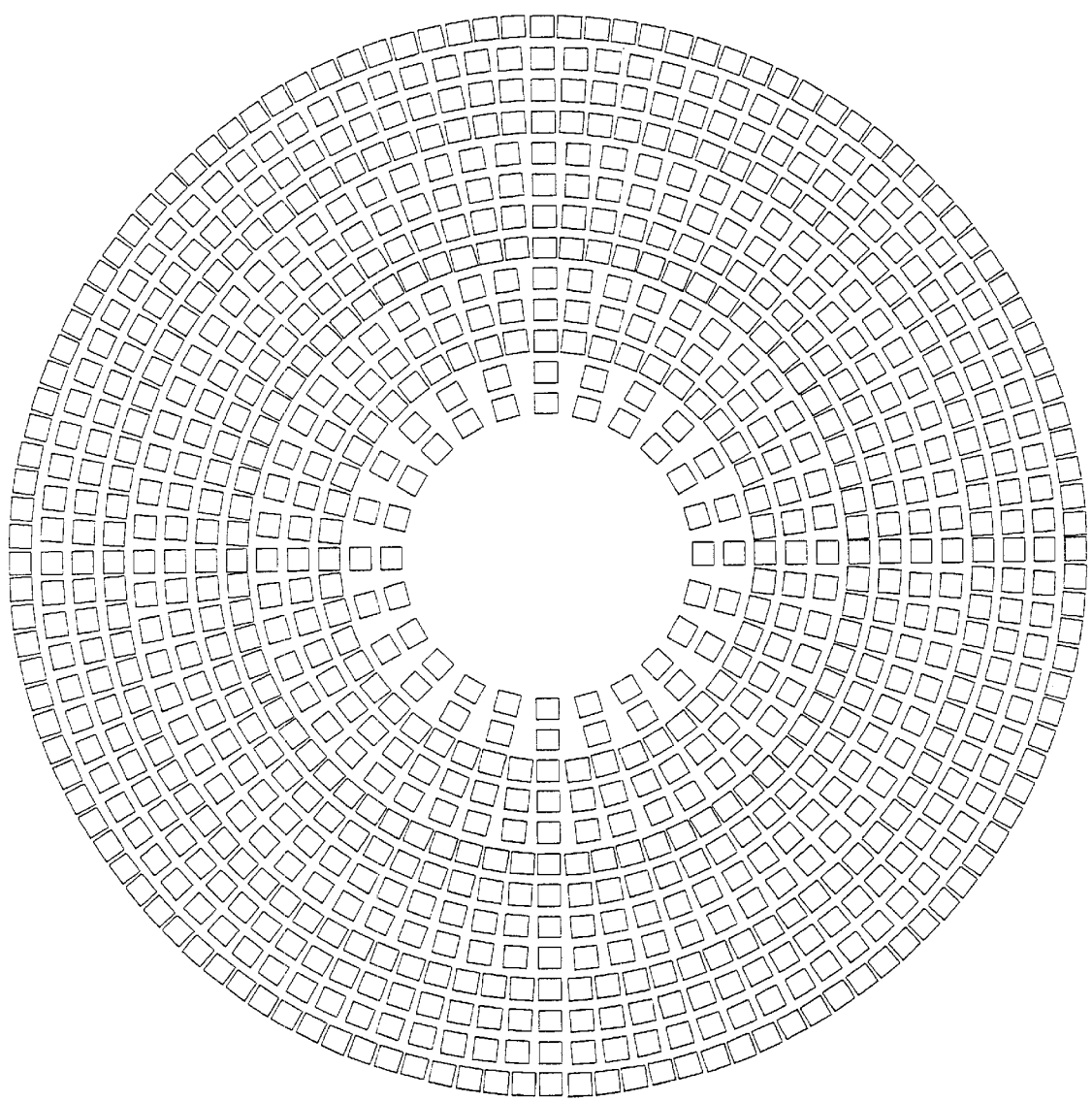
FIG. 9 is a plan view showing a further construction example of the sensor.

Also, FIG. 9 shows a construction of a sensor in which each pixel has a quadrangular or square shape and has the same size. In this construction, the size of each pixel is constant regardless of a position of the radial direction of the sensor so that the difference in sensitivity of each ring band is eliminated.

Figure 10:
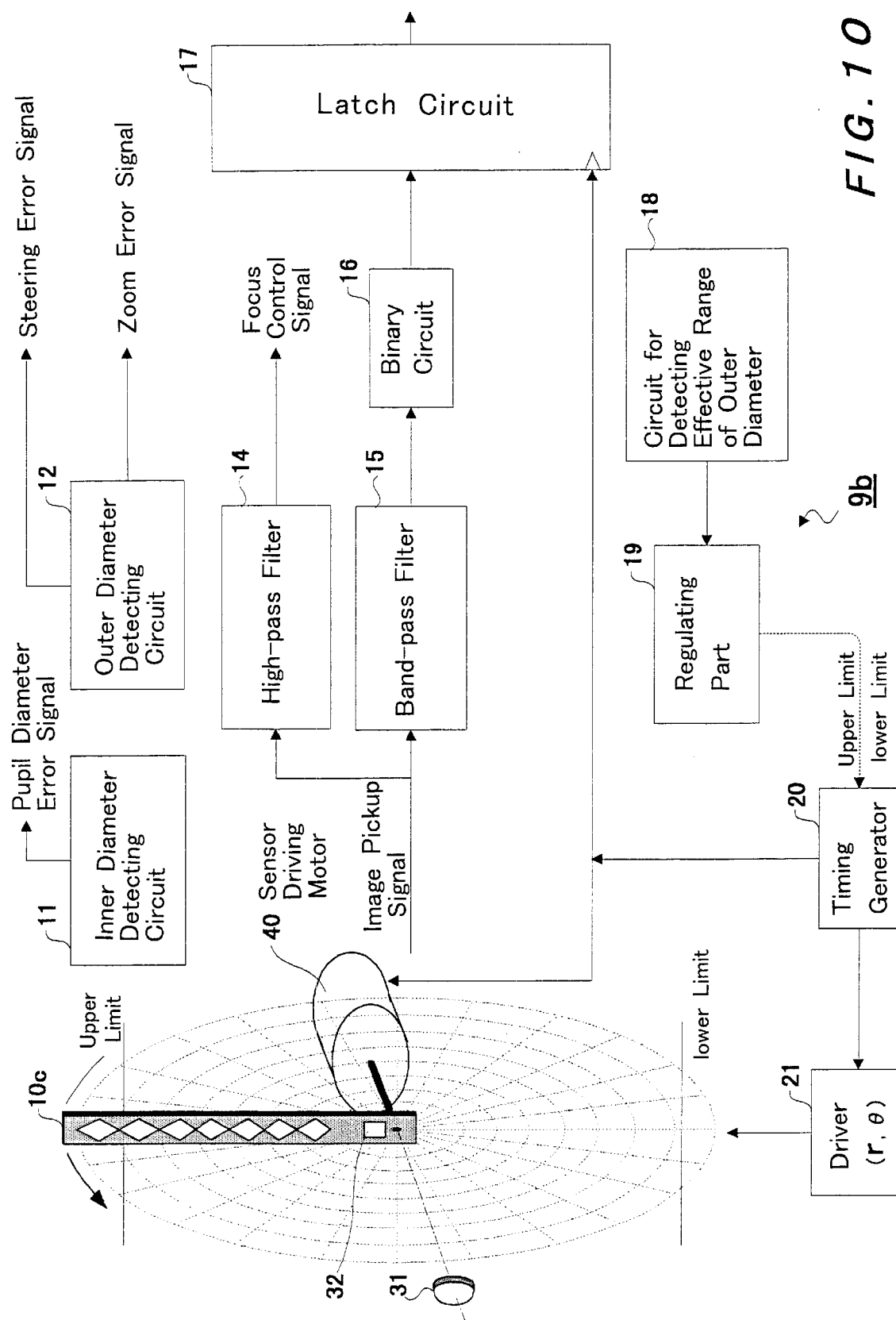
FIG. 10 is a block diagram showing a further construction example of the iris sensor part.

Next, a third embodiment will be described with reference to FIG. 10. FIG. 10 shows a construction of an iris sensor part 9b of an iris recognition system according to the third embodiment. The iris sensor part 9b is different from the iris sensor part 9a shown in FIG. 5 in that a sensor 10c which is rotated and driven is used instead of the sensor 10a. The other constructions are the same as those of the second embodiment and have the same reference characters.

In FIG. 10, the sensor 10c is not an area sensor such as the sensors 10, 10a and 10b but a line sensor or a linear sensor. The sensor 10c synchronously rotates about the axis corresponding to the center of the sensors 10, 10a and 10b by a sensor driving motor 40, and a detection equivalent to that of the area sensor such as the sensors 10, 10a and 10b is performed by one rotation. This synchronous rotation is to rotate in synchronization with a timing pulse fed from a timing generator 20 and so on. Also, when a pixel signal from the sensor 10c is picked up, the sensor 10c is rotating so that the pixel signal is outputted using a rotary transformer or a sliding brush and so on.

The pixels of the sensor 10c are formed in the rhombic shape having the diagonal in the radial direction like FIG. 7. The reason why this rhombic shape is adopted is because an operation processing of the weighting is eliminated as described above.

Also, the length of the radial direction of the rhombic pixel as described above may be varied according to the rate of stretching and shrinking of the iris.

Though the third embodiment has some complicated construction in comparison with the first and second embodiments, the sensor 10c may be constructed simply and readily in comparison with the sensors 10, 10a and 10b.

Also, the construction using the linear sensor may be applied to the first embodiment. In this case, each pixel of the linear sensor may not have the rhombic shape and, for example, may have the rectangular shape or the other shapes.

Next, a fourth embodiment will be described. In the first embodiment to the third embodiment, all the image pickup signals are outputted from the sensors 10, 10a to 10c directly and the edge image is obtained through the band-pass filter 15, and the iris code formed in the binary format by the binary circuit 16 is outputted. On the contrary, the fourth embodiment is intended to output the edge image directly by the sensor and the iris code is obtained by converting this outputted signal into the binary format by the binary circuit 16.

Thus, in the fourth embodiment, the band-pass filter 15 in the first embodiment to the third embodiment is eliminated, and the construction of the circuits 11 and 12 for detecting the inner and outer diameters of the iris, the high-pass filter 14, and the circuit 18 for detecting the effective range of the outer diameter of the iris which perform a processing on the basis of the edge image is also simplified so that a processing load may be reduced.

This construction of the sensor for directly outputting the edge image is achieved by an optical edge processing using an artificial retina lens disclosed in, for example, Japanese Patent Laid-Open Publication No.5-297325. That is, it is constructed so as to receive light inputted to each pixel in the first embodiment to the third embodiment through a spatial frequency filter and such a construction is an idea of "eye for eye" as it were.

Though a feature extraction of the iris is optically performed in the above example, this feature extraction may be electrically performed. For example, an outline detecting circuit which is adopted in a neurochip devised by C. A. Mead et al. in California Institute of Technology (see C. A. Mead and M. A. Mahowald, "A Silicon Model of Early Visual Processing", Neural Networks, vol.1, pp.91–97 of 1988) and imitates primary sight of the human may be used for this purpose.

Figure 11:
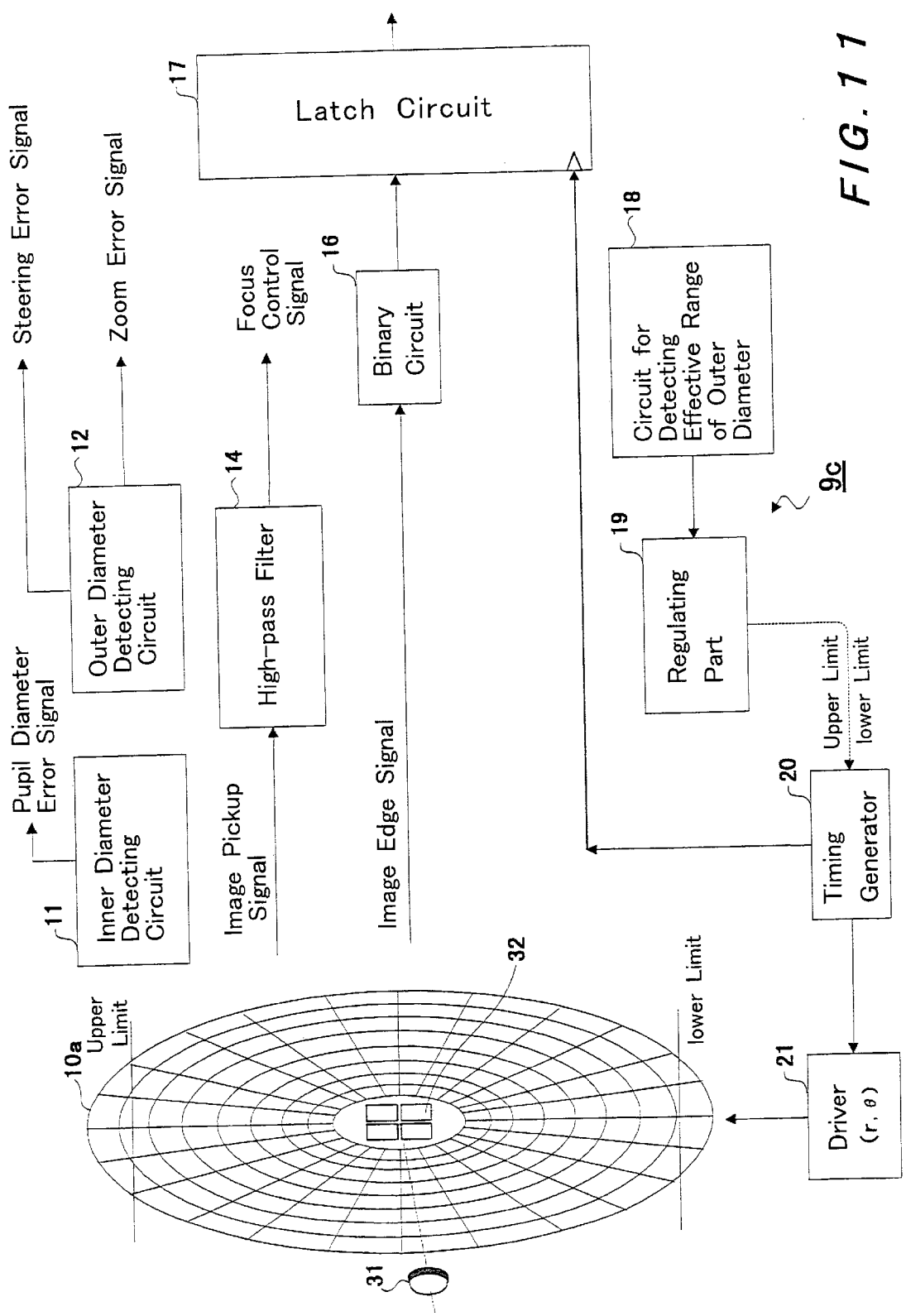
FIG. 11 is a block diagram showing still a further construction example of the iris sensor part.

FIG. 11 shows a construction example of an iris sensor part using such a sensor. The construction shown in FIG. 11 has no construction for converting an image and extracting an edge image, and in the construction, an image edge signal obtained from the sensor is formed in a binary format directly by the binary circuit 16 and an iris code is inputted to a latch 17. Thus, no band-pass filter 15 shown in the construction of FIG. 5 is required.

Figure 12:
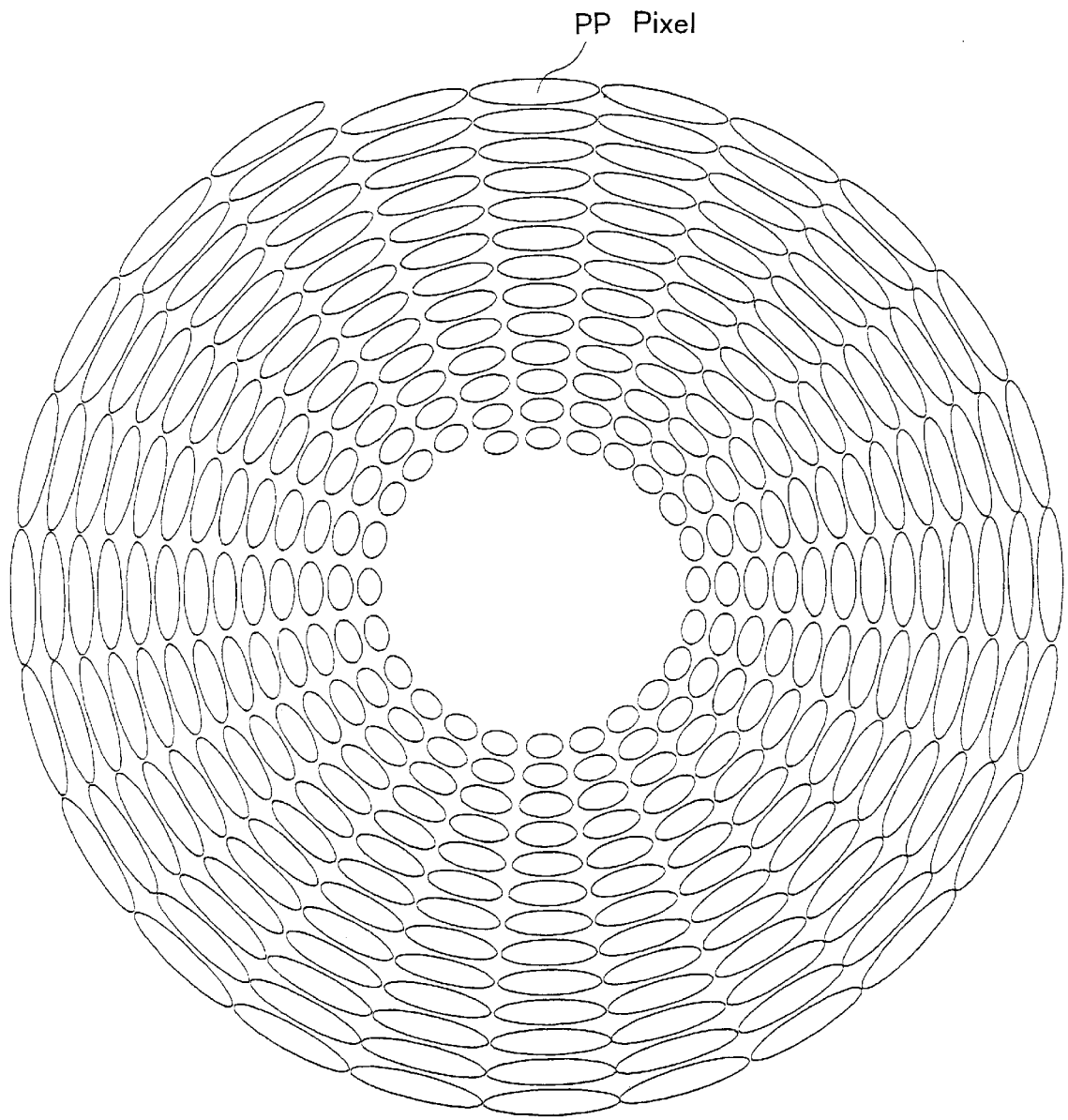
FIG. 12 is a plan view showing a further construction example of the sensor.

Also, although all the sensors have the pixel array pattern of polar coordinate type in each embodiment described above, the sensor is not limited to this pattern and, for example, as shown in FIG. 12, the sensor may have a pattern in which pixels PP are arranged in a spiral shape from the inner diameter of the iris of the sensor.

In the case of the sensor having this spiral array pattern, since the sensor functions as an one-dimensional sensor, a processing may be performed so as not to be affected by the variation in the pupil diameter, for example, by assigning serial numbers to each pixel from the outer circumference and detecting that the pixels from No.1 to No.N are the iris portion and normalizing said pixels with N. In this case, particularly, read control of each pixel is simplified. Also, even for the sensor of polar coordinate type, an one-dimensional read scan may be implemented by joining the pixels of each concentric circle in the same manner of the spiral sensor.

Further, in the case of taking the iris image as a color sensor in which the pixels are arranged in the spiral shape with three R, G, B, addressing of each pixel forming the iris portion is facilitated.

The construction capable of obtaining the iris code from the sensor part for the iris recognition system has been described hereinbefore. On the contrary, by incorporating a comparison circuit for comparing the detected iris code with a predetermined code into a sensor chip itself and incorporating a nonvolatile memory capable of registering the iris codes for comparison to some degree simultaneously, it may be constructed so as to output not the iris code but the comparison result, namely the identification result (for example, OK or NG) from the sensor part. In this case, this output is preferably ciphered or encoded to feed in order to secure security. By such a construction, a small identification apparatus used instead of keys of house, room, car, etc. may be implemented by only this chip, with the result that range of application may be extended.

Also, since it is supposed that iris detection of facing type may be used, the construction may be simplified using relative parallel translation of a VAP (vertical angle variable prism) or a plurality of lenses instead of preprocessing such as alignment of the iris by the wide-angle cameras mentioned above. For example, in the case of using the VAP as shown in FIG. 13, the iris image may be obtained by control of only an optical system including the vertical angle variable prism 8a and a zoom lens 8b and a zoom camera including an iris sensor part 9c.

Figure 13:
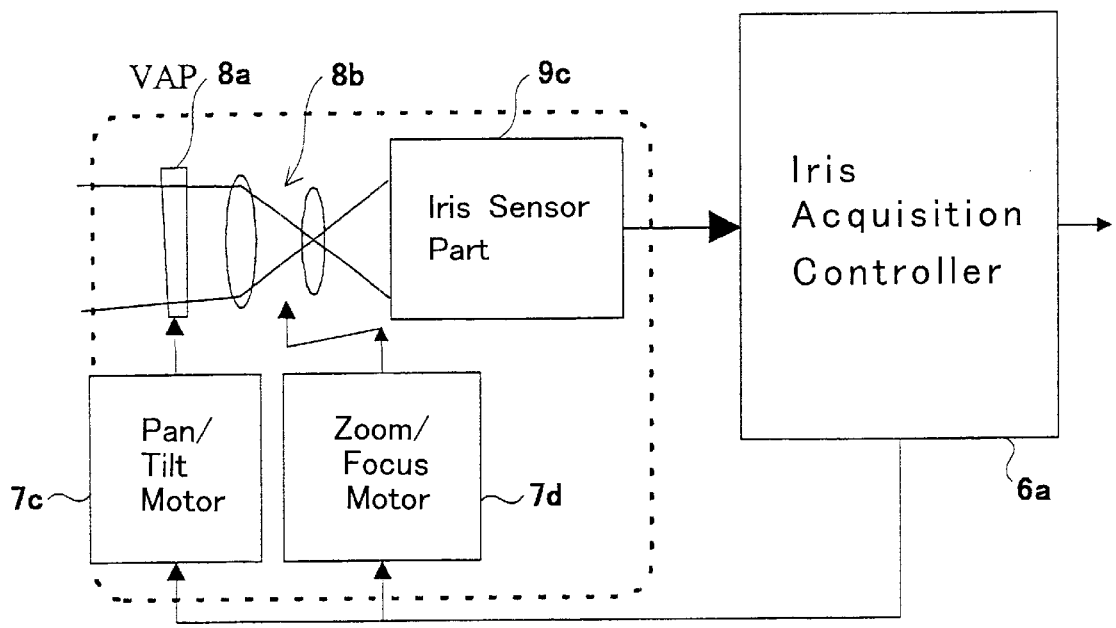
FIG. 13 is a block diagram showing a schematic construction of the iris recognition system according to another embodiment of the present invention.

Also, in FIG. 13, the numeral 7c designates a pan/tilt motor for driving the prism 8a and the numeral 7d designates a zoom/focus motor. Also, the numeral 6a designates an iris acquisition controller and a control part of the wide-angle cameras as the iris acquisition controller 6 shown in FIG. 1 is not required so that the controller 6a is simplified.

Figure 14:
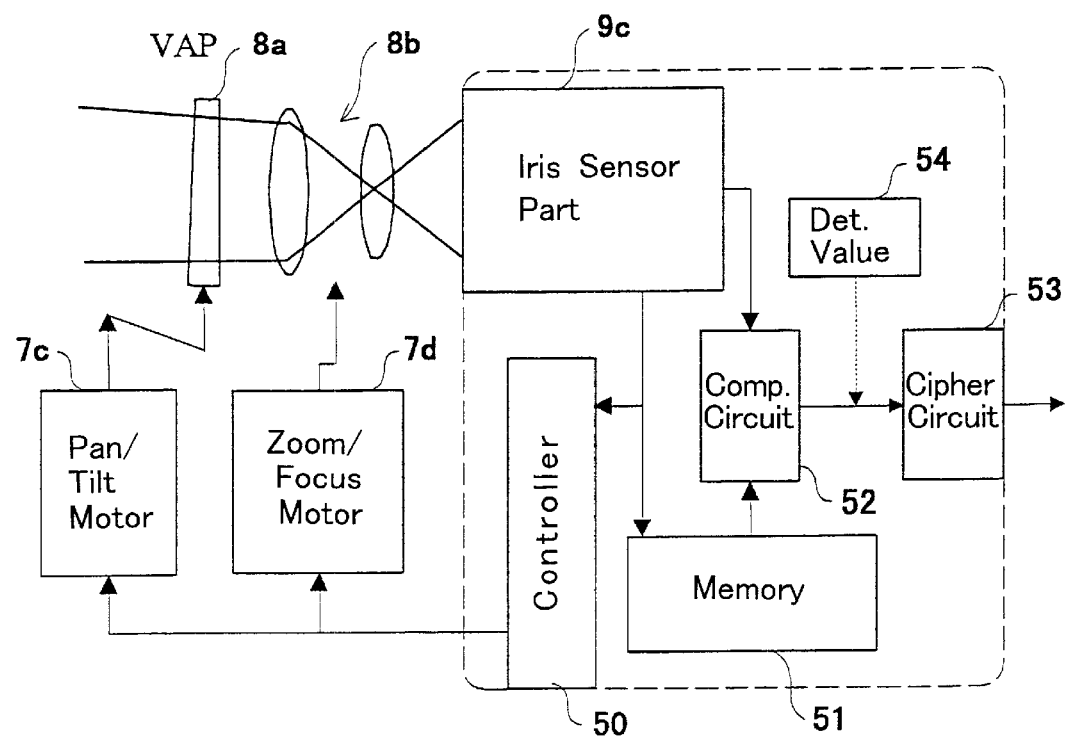
FIG. 14 is a block diagram showing a schematic construction of the iris recognition system according to a further embodiment of the present invention.

Further, FIG. 14 shows a construction in which a controller 50 for driving and controlling the VAP 8a and the zoom lens 8b, a memory 51 for storing the iris code for comparison, a comparison circuit 52 for comparing the detected iris code with the iris code stored in the memory, and a cipher circuit 53 are integrated into one chip. By such a construction, the cost necessary for the iris recognition system may be reduced more. Any memory device such as a hard disk unit, a magnet-optical disk unit other than the nonvolatile semiconductor memory may be used as the memory 51.

Also, it is possible to make identification determining level, that is, threshold of correlation degree of iris codes, adjustable. For example, in FIG. 14, a determination value register 54 is provided. A determination value indicating an identification determining level can be stored in the determination value register 54, for example, from external, to designate a required correlation level. Also, it is possible to selectively supply one of a plurality of determination values from external to the determination value register 54.

It is also possible to provide a plurality of determination value registers and a selecting circuit for selecting one of the outputs of the registers.

It is further possible to make the identification determination level adjustable internally, for example, based on the determination value supplied from a microprocessor in the iris recognition system. The microprocessor may generate the determination value, for example, depending on various conditions, such as brightness of the location the iris recognition system is installed, required precision of recognition, and the like.

In the above embodiment of facing type, it may be constructed so that a three-dimensional alignment processing, which has been performed by the wide-angle cameras 1a and 1b, to the zoom lens 8b is performed by approach of the subject to a predetermined distance and position from the apparatus, and only fine adjustment to perform positioning and focusing so as to direct the optical axis of the zoom lens 8b precisely toward the position of the eye using the known VAP 8a is controlled by the iris acquisition controller or the sensor part itself.

The margin of range of such a predetermined position is about ±3 cm in a distance of 25 to 30 cm from the apparatus, so-called, a distance of distinct vision. Further, in the case of providing an illuminating LED on the optical axis of the sensor, the pupil diameter may be adjusted simultaneously if the subject is asked to look this LED.

Also, it is obvious that a method in which a person peeps into the zoom lens 8b from a given window etc. may be adopted without a method for facing at the distance of distinct vision. The difference between the facing method and the peeping method is that a focal length of the image pickup lens 8b only differs. Also, the lens 8b may not always be a zoom lens and may be a lens with single focal point or a lens capable of switching the focal length.

Particularly, when a screen of a personal computer may be used in the personal recognition of electronic business, focusing may be performed even using a camera with a fixed focal point etc. by displaying an iris image and a cross line on the screen to perform steering, and displaying a message of "please approach the screen a little", for example.

In this case, practically, the iris image is obtained by attaching an adapter lens to a normal camera mounted in the personal computer as an attachment or an option other than a method for attaching a dedicated camera to the iris recognition system, and coordinate transformation is performed by a software of the personal computer and the iris code may be obtained. Also, the iris code may be obtained by connecting a dedicated sensor and a normal CCD/MOS sensor to the iris recognition system through a half mirror and mounting both the sensors.

Also, it is possible to construct a band-pass filter using a normal LCR and compare output of the band-pass filter with a predetermined threshold value by a comparator to form in a binary format. On the contrary, a function equivalent to the construction including the band-pass filter and the comparator may be achieved by calculating the average of outputs of continuous N pixels and comparing this average with output of a target pixel. In this case, a comparison processing may be executed without being affected by a scan speed, and also, a bandwidth of the band-pass filter may be varied by selecting the value of N, so that more flexible processing may be performed. Also, the continuous N pixels may be selected from the range including the pixels to be compared or from backward and forward of the range including the pixels to be compared.

In the above description, the method has been mainly described in which features of the tangential direction of the iris are extracted by scanning in the tangential direction of the sensor. However, in the present invention, it is preferable that scanning is also performed in the radial direction to extract features of its direction. But, since generally a spatial frequency of the radial direction is not too high judging from the feature of the iris pattern, resolving power is reduced by taking a weighted mean of the tangential direction according to this (for example, 32 division) and the scanning in the radial direction is performed, so that redundancy may be reduced favorably.

Further, in this case, it is unnecessary to increase the resolving power (for example, 16 division) of the radial direction too. Anyway, a circuit construction like the circuit construction used for scanning in the tangential direction may be used to perform the scanning in the radial direction. Particularly, in the case of constructing the band-pass filter by the comparison with the average of the N pixels, it may also be used as the band-pass filter in the radial direction.

It is also possible to perform scanning only in the tangential direction. Also, it is possible to perform scanning in the tangential direction in a ring band and check if sufficient iris information is obtained to perform identification. If sufficient iris information has not yet been obtained, it is possible to scan in the tangential direction of the next ring band.

The above-mentioned embodiments or the modifications may be combined respectively if desired. Further, the present invention may be applied to the eye of human as well as animals generally and, for example, individual identification thereof may be performed.

As described in detail above, since the present invention uses an image pickup sensor comprising a group of pixels arranged in polar coordinates, it is unnecessary to transform an orthogonal coordinate system into a polar coordinate system in order to obtain an iris code, and the iris code may be generated at high speed without a dedicated processor, so that time necessary for personal identification may be saved and a load of a processing apparatus may be reduced.

Also, since no apparatus for performing coordinate transformation is required, miniaturization and weight-saving of a system may be improved.

Also, since an image of an iris portion with the same size always may be acquired by using means for regulating light, an information processing of the iris portion is facilitated and particularly, a check processing using a pattern matching may also be performed.

Also, when a device for detecting edge information electrically or optically is used as the image pickup sensor, a load necessary for generation processing of the iris code is reduced and the processing may be performed at high speed and further, miniaturization and weight-saving of the system may be promoted.

Further, by forming the pixels of the image pickup sensor in approximately rhombic shape, it is unnecessary to perform compensation of sensitivity and weighting, with the result that the load necessary for generation processing of the iris code may be reduced and the time may be saved.

Still further, since pixel density of the radial direction is varied according to rate of stretching and shrinking of the iris, the decrease in recognition rate accompanying the stretching and shrinking of the iris may be prevented.

In the foregoing specification, the invention has been described with reference to specific embodiments. However, one of ordinary skill in the art appreciates that various modifications and changes can be made without departing from the scope of the present invention as set forth in the claims below. Accordingly, the specification and figures are to be regarded in an illustrative sense rather than a restrictive sense, and all such modifications are to be included within the scope of the present invention. Therefore, it is intended that this invention encompasses all of the variations and modifications as fall within the scope of the appended claims.

What is claimed is:

1. An iris information sensor comprising:
   an image pickup sensor having a group of photoelectric conversion pixels arranged in polar coordinates;
   a focuser that focuses image light from an iris region of an eye on the image pickup sensor so that the center of an iris image formed on the sensor substantially matches with the pole of the polar coordinates of the sensor; and
   a scanner that sequentially scans the photoelectric conversion pixels of the sensor to read out an iris image signal.

2. The iris information acquisition apparatus as defined in claim 1, wherein the image pickup sensor comprises a group of pixels arranged in concentric circles.

3. The iris information acquisition apparatus as defined in claim 1, wherein the image pickup sensor comprises a group of pixels arranged in a spiral shape extending in the radial direction.

4. An iris information acquisition apparatus for obtaining image information of an iris region, comprising:
   an image pickup sensor having a group of photoelectric conversion pixels arranged in polar coordinates;
   an image pickup optical focuser that focuses image light from the iris region on the image pickup sensor;
   an optical axis operation controller that substantially matches the center of an iris image formed on the sensor with the pole of the polar coordinates of the sensor;
   a region determiner that determines the iris region by acquiring the inner and outer diameters of the iris according to an iris image signal obtained by the sensor; and
   a read scanner that scans the determined iris region in a predetermined sequence and obtains an output value corresponding to information of the iris region.

5. The iris information acquisition apparatus as defined in claim 4, wherein said read scanner scans the determined iris region at least in the tangential direction.

6. The iris information acquisition apparatus as defined in claim 4, wherein said read scanner that scans the determined iris region, scans the determined iris region in the tangential and radial directions at predetermined intervals.

7. The iris information acquisition apparatus as defined in claim 4, wherein said read scanner divides the determined iris region into predetermined concentric ring bands, determines the number of pixels in the radial direction of each ring band and reads the output value corresponding to information of each ring band in which a weighted mean is performed according to the number of pixels.

8. The iris information acquisition apparatus as defined in claim 4, wherein said region determiner determines the iris region according to an amplitude of a feature extraction signal, said feature extraction signal obtained by passing the image signal through a band-pass filter, said image signal obtained by scanning the image pickup sensor in the tangential direction.

9. The iris information acquisition apparatus as defined in claim 4, wherein said region determiner determines the iris region according to level variation in the image signal obtained by the scan in the radial direction of the image pickup sensor.

10. The iris information acquisition apparatus as defined in claim 4, wherein said optical axis operation controller calculates the direction and size of an error between the center of the iris image formed on the image pickup sensor and the pole of the polar coordinates of the sensor to control a matching of the center of the iris image with the pole of the polar coordinates of the sensor, by further passing the feature extraction signal through a low-pass filter, said feature extraction signal obtained by passing the image signal through the band-pass filter, said image signal obtained by scanning the image pickup sensor in the tangential direction.

11. The iris information acquisition apparatus as defined in claim 4, further comprising an illuminator that irradiates illumination light to the eye and a group of light receiving elements that receive reflected illumination light from the eye, said optical axis operation controller controlling a matching of the center of the iris image with the pole of the polar coordinates of the image pickup sensor according to an amount of receiving light of the group of light receiving elements.

12. The iris information acquisition apparatus as defined in claim 4, further comprising an iris code generator that generates an iris code according to the output value read by the read scanner.

13. The iris information acquisition apparatus as defined in claim 4, wherein said optical axis operation controller controls a matching of the center of the iris image formed on the image pickup sensor by moving a mirror placed in an optical path between the iris of the eye of a subject and the sensor with the pole of the polar coordinates of the sensor.

14. The iris information acquisition apparatus as defined in claim 4, wherein said optical axis operation controller controls a matching of the center of the iris image formed on the image pickup sensor by moving the sensor with the pole of the polar coordinates of the sensor.

15. The iris information acquisition apparatus as defined in claim 4, wherein said optical axis operation controller controls a matching of the center of the iris image formed on the image pickup sensor by a vertical angle variable prism placed in an optical path between the iris of the eye of a subject and the sensor with the pole of the polar coordinates of the sensor.

16. The iris information acquisition apparatus as defined in claim 4, wherein said optical axis operation controller controls a matching of the center of the iris image formed on the image pickup sensor by mutually translating a plurality of lenses placed in an optical path between the iris of the eye of a subject and the sensor with the pole of the polar coordinates of the sensor.

17. The iris information acquisition apparatus as defined in claim 4, wherein said image pickup sensor comprises a linear sensor in which pixels are arranged in the radial direction and a rotation driver that synchronously rotates the linear sensor around the pole of the polar coordinates, and a function equivalent to the group of the pixels of the polar coordinates is achieved by the rotation of the linear sensor through the rotation driver.

18. The iris information acquisition apparatus as defined in claim 4, wherein each pixel of the image pickup sensor comprises one of a MOS sensor and a CCD sensor.

19. The iris information acquisition apparatus as defined in claim 4, wherein each pixel of the image pickup sensor comprises a detector that detects edge information one of electrically and optically.

20. The iris information acquisition apparatus as defined in claim 4, wherein pixel density in the radial direction of each pixel of the image pickup sensor corresponds to the rate of stretching and shrinking of the iris.

21. The iris information acquisition apparatus as defined in claim 4, wherein the image pickup sensor comprises a group of pixels arranged in a spiral shape extending in the radial direction.

22. An iris information acquisition apparatus for obtaining image information of an iris region of the eye, comprising:
   an image pickup sensor comprising a group of photoelectric conversion pixels arranged in polar coordinates;
   an image pickup optical focuser that focuses image light from the iris region on the image pickup sensor;
   an illuminator that irradiates illumination light to the eye having the iris;
   an optical axis operation controller that substantially matches the center of an iris image formed on the sensor with the pole of the polar coordinates of the sensor;
   a light adjustment controller that controls the inner diameter of the iris image formed on the sensor by irradiating visible light to the eye having the iris from the illuminator, adjusting an amount of the light and defining the pupil diameter; and
   a read scanner that scans the sensor in a predetermined sequence and reads image information of the iris region.

23. The iris information acquisition apparatus as defined in claim 22, wherein said read scanner scans the determined iris region at least in the tangential direction.

24. The iris information acquisition apparatus as defined in claim 22, wherein said read scanner scans the determined iris region in the tangential and radial directions at predetermined intervals.

25. The iris information acquisition apparatus as defined in claim 22, wherein said image pickup optical focuser comprises a zoom lens, the zoom lens ensuring that the outer diameter of the iris image is formed on the image pickup sensor.

26. The iris information acquisition apparatus as defined in claim 22, wherein each pixel of the image pickup sensor has a light receiving region with an approximately rhombic shape having each diagonal in the radial and tangential directions of the polar coordinates.

27. The iris information acquisition apparatus as defined in claim 22, wherein each pixel of the image pickup sensor is also arranged in a region with an approximately rhombic shape surrounded by the light receiving regions with the approximately rhombic shape.

28. The iris information acquisition apparatus as defined in claim 22, further comprising an iris code generator that generates an iris code according to the output value read by the read scanner.

29. The iris information acquisition apparatus as defined in claim 28, wherein said iris code generator comprises a comparitor that compares a band-pass filter receiving the output value and output of the band-pass filter with a predetermined threshold value.

30. The iris information acquisition apparatus as defined in claim 28, wherein said iris code generator generates the iris code by comparing the output value of a plurality of continuous pixels with output of a target pixel.

31. The iris information acquisition apparatus as defined in claim 28, wherein information on the effective range of the iris region is added to the iris code.

32. The iris information acquisition apparatus as defined in claim 28, wherein information on resolution of the image pickup sensor is added to the iris code.

33. The iris information acquisition apparatus as defined in claim 28, wherein information on tilt of the eye is added to the iris code.

34. The iris information acquisition apparatus as defined in claim 28, wherein information on whether the iris code is the right eye or the left eye is added to the iris code.

35. The iris information acquisition apparatus as defined in claim 22, further comprising a group of light receiving elements that receive reflected light from the eye by said illuminator, said optical axis operation controller controls a matching of the center of the iris image with the pole of the polar coordinates of the image pickup sensor according to an amount of receiving light of the group of light receiving elements.

36. The iris information acquisition apparatus as defined in claim 22, wherein said optical axis operation controller calculates the direction and size of an error between the center of the iris image formed on the image pickup sensor and the pole of the polar coordinates of the sensor to control a matching of the center of the iris image with the pole of the polar coordinates of the sensor, by further passing a feature extraction signal through a low-pass filter, said feature extraction signal obtained by passing the image signal through the band-pass filter, said image signal obtained by scanning the image pickup sensor in the tangential direction.

37. The iris information acquisition apparatus as defined in claim 22, wherein said optical axis operation controller controls a matching of the center of the iris image formed on the image pickup sensor by moving a mirror placed in an optical path between the iris of the eye of a subject and the sensor with the pole of the polar coordinates of the sensor.

38. The iris information acquisition apparatus as defined in claim 22, wherein said optical axis operation controller controls a matching of the center of the iris image formed on the image pickup sensor by-moving the sensor with the pole of the polar coordinates of the sensor.

39. The iris information acquisition apparatus as defined in claim 22, wherein said optical axis operation controller controls a matching of the center of the iris image formed on the image pickup sensor by a vertical angle variable prism placed in an optical path between the iris of the eye of a subject and the sensor with the pole of the polar coordinates of the sensor.

40. The iris information acquisition apparatus as defined in claim 22, wherein said optical axis operation controller controls a matching of the center of the iris image formed on the image pickup sensor by mutually translating a plurality of lenses placed in an optical path between the iris of the eye of a subject and the sensor with the pole of the polar coordinates of the sensor.

41. The iris information acquisition apparatus as defined in claim 22, wherein said image pickup sensor comprises a linear sensor in which pixels are arranged in the radial direction and a rotation driver that synchronously rotates the linear sensor around the pole of the polar coordinates, and a function equivalent to the group of the pixels of the polar coordinates is achieved by the rotation of the linear sensor through the rotation driver.

42. An iris information acquisition apparatus as defined in claim 22, wherein each pixel of the image pickup sensor comprises one of a MOS sensor and a CCD sensor.

43. The iris information acquisition apparatus as defined in claim 22, wherein each pixel constructing the image pickup sensor comprises a detector that detects edge information one of electrically and optically.

44. The iris information acquisition apparatus as defined in claim 22, wherein pixel density in the radial direction of each pixel of the image pickup sensor corresponds to the rate of stretching and shrinking of the iris.

45. The iris information acquisition apparatus as defined in claim 22, wherein the image pickup sensor comprises a group of pixels arranged in a spiral shape extending in the radial direction.

46. An iris identification apparatus for acquiring an iris code representing information of an iris region of the eye and comparing and matching the acquired iris code with a previously registered iris code, comprising:
   an image pickup sensor comprising a group of photoelectric conversion pixels arranged in polar coordinates;
   an image pickup optical focuser that focuses image light from the iris region on the image pickup sensor;
   an optical axis operation controller that substantially matches the center of an iris image formed on the sensor with the pole of the polar coordinates of the sensor;
   a region determiner that determines the iris region by acquiring the inner and outer diameters of the iris according to an iris image signal obtained by the sensor;
   a read scanner that divides the determined iris region into predetermined concentric ring bands and determines the number of pixels in the radial direction of each ring band and reads the output value corresponding to information of each ring band in which weighted mean is performed according to the number of pixels;
   an iris code generator that generates the iris code according to the output value; and
   a comparitor that matches the generated iris code with the previously registered iris code.

47. The iris identification apparatus as defined in claim 46, wherein said comparitor that matches the iris region including a region hidden by the eyelids.

48. The iris identification apparatus as defined in claim 46, further comprising a nonvolatile memory that stores the previously registered iris code, and one of an encoder that encodes and a cipher that ciphers the matched result in order to provide security.

49. The iris identification apparatus as defined in claim 48, further comprising an adjuster that adjusts the identification determination level used when matching the generated iris code with the previously registered iris code.

50. An iris identification apparatus that acquires information of an iris region of the eye and compares and matches the acquired information of the iris region with information of an iris region registered previously, comprising:
   an image pickup sensor comprising a group of photoelectric conversion pixels arranged in polar coordinates;
   an image pickup optical focuser that focuses image light from the iris region on the image pickup sensor;
   an illuminator that radiates illumination light to the eye having the iris;
   an optical axis operation controller that substantially matches the center of an iris image formed on the sensor with the pole of the polar coordinates of the sensor;

a light adjustment controller that controls the inner diameter of the iris image formed on the sensor by irradiating visible light to the eye having the iris from the illuminator, adjust an amount of the light and defines the pupil diameter;

a read scanner that scans the sensor in the tangential and radial directions and reads the information of the iris region; and a matcher that matches the information of the iris region read by the read scanner with the information of the iris region registered previously through pattern matching.

51. The iris identification apparatus as defined in claim 50, wherein said image pickup optical focuser includes a zoom lens, the zoom lens ensuring that the outer diameter of the iris image is formed on the image pickup sensor.

52. The iris identification apparatus as defined in claim 50, wherein the matcher matches the iris region including a region hidden by the eyelids.

53. The iris identification apparatus as defined in claim 50, further comprising a nonvolatile memory that stores the previously registered iris code, and one of an encoder that encodes and a cipher that ciphers the matched result in order to provide security.

54. The iris identification apparatus as defined in claim 53, further comprising an adjuster that adjusts an identification determination level used when said matcher performs said matching.

55. An iris identification method for acquiring an iris code representing information of an iris region of the eye and comparing and matching the acquired iris code with a previously registered iris code, comprising:

using an image pickup sensor comprising a group of photoelectric conversion pixels arranged in polar coordinates;

focusing image light from the iris region on the image pickup sensor through an image pickup optical system;

substantially matching the center of an iris image formed on the sensor with the pole of the polar coordinates of the sensor through an optical axis operation controller;

determining the iris region by acquiring the inner and outer diameters of the iris according to an iris image signal obtained by the sensor;

dividing the determined iris region into predetermined concentric ring bands, determining the number of pixels in the radial direction of each ring band and reading the output value, corresponding to information of each ring band in which a weighted mean is calculated according to the number of pixels;

generating the iris code from the output value through an iris code generator; and performing personal identification by matching the generated iris code with the previously registered iris code.

56. The iris identification method as defined in claim 55, wherein the iris region, including a region hidden by the eyelids, is matched.

57. The iris identification method as defined in claim 55, wherein the previously registered iris code is stored in a nonvolatile memory, and further comprising one of encoding and ciphering the matched result in order to provide security.

58. The iris identification method as defined in claim 57, wherein an identification determination level, when performing personal identification, is adjustable.

59. An iris identification method for acquiring information of an iris region of the eye and comparing and matching the acquired information of the iris region with information of an iris region registered previously, comprising:

using an image pickup sensor comprising a group of photoelectric conversion pixels arranged in polar coordinates;

focusing image light from the iris region on the image pickup sensor through an image pickup optical system;

irradiating illumination light to the eye having the iris through an illuminator;

substantially matching the center of an iris image formed on the sensor with the pole of the polar coordinates of the sensor through an optical axis operation controller;

controlling the inner diameter of the iris image formed on the sensor by irradiating visible light to the eye having the iris from the illuminator, adjusting an amount of the light and defining the pupil diameter;

scanning the sensor in the tangential and radial directions and reading the information of the iris region through a read scanner; and performing personal identification by matching the information of the iris region read by the read scanner with the information of the iris region registered previously through pattern matching.

60. The iris identification method as defined in claim 59, wherein said image pickup optical system includes a zoom lens, the zoom lens ensuring that the outer diameter of the iris image is formed on the image pickup sensor.

61. The iris identification method as defined in claim 59, wherein the iris region, including a region, hidden by the eyelids, is matched.

62. The iris identification method as defined in claim 59, wherein the previously registered iris code is stored in a nonvolatile memory, and further comprising one of encoding and ciphering the matched result in order to provide security.

63. The iris identification method as defined in claim 62, wherein an identification determination level, when performing personal identification, is adjustable.

64. An iris information sensing method using an iris image pickup sensor having a group of photoelectric conversion pixels arranged in polar coordinates, the method comprising:

focusing image light from an iris of an eye on the image pickup sensor so that the center of an iris image formed on the sensor substantially matches with the pole of the polar coordinates of the sensor; and sequentially scanning the photoelectric conversion pixels of the sensor to read out an iris image signal.

* * * * *